(12) United States Patent
Gygax et al.

(10) Patent No.: US 8,021,846 B2
(45) Date of Patent: Sep. 20, 2011

(54) **METHOD FOR DETERMINING AZOLE RESISTANCE IN *CANDIDA GLABRATA***

(75) Inventors: Scott E. Gygax, Bordentown, NJ (US); John-Paul Vermitsky, Philadelphia, PA (US); Sean G. Chadwick, Florence, NJ (US); Matthew J. Self, Westmont, NJ (US); Eli Mordechai, Robbinsville, NJ (US); Martin E. Adelson, Belle Mead, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days.

(21) Appl. No.: 12/381,492

(22) Filed: Mar. 12, 2009

(65) Prior Publication Data

US 2009/0305274 A1 Dec. 10, 2009

Related U.S. Application Data

(60) Provisional application No. 61/069,105, filed on Mar. 12, 2008.

(51) Int. Cl.
*C12Q 1/68* (2006.01)
(52) U.S. Cl. .................. 435/6.12; 536/24.32; 536/24.33
(58) Field of Classification Search ............. 435/6, 91.2, 435/6.12; 536/24.32, 24.33
See application file for complete search history.

(56) References Cited

OTHER PUBLICATIONS

Sanguinetti, M. et al. Mechanisms of azole resistance in clinical isolates of Candida glabrata collected during a hospital survey of antifungal resistance. Antimicrobial Agents and Chemotherapy, vol. 40, No. 2, pp. 668-679, 2005.*
Sanglard, D. et al. The ATP binding cassette transporter gene CgCDR1 from Candida glabrata is involved in the resistance of clinical isolates to azole antifungal agents. Antimicrobial Agents and Chemotherapy, vol. 43, No. 11, pp. 2753-2765, 1999.*
Kofla, G. et al. Development of a new real-time Taqman PCR assay for quantitative analyses of Candida albicans resistance genes expression. J Microbiological Methods, vol. 68, pp. 178-183, 2007.*
Lee, Mi-Kyung et al. Drug resistance genes and trailing growth in Candida albicans isolates. J. Antimicrobial Chemotherapy, vol. 53, pp. 217-224, 2004.*
Ostrosky-Zeichner, L. et al. Antimicrob. Agents Chemother. 47: 3149-3154, 2003.
Komshian, S.V. et al. Rev. Infect. Dis. 11: 379-390, 1989.
Fidel, P.L. et al. Clin. Microbiol. Rev. 9:335-348, 1996.
Vermitsky, J.-P. et al. J. Clin. Microbiol. 46(4): 1501-1503, 2008.
Richter, S.S. et al. J. Clin Microbiol. 45(5): 2155-2162, 2005.
Nat. Com. for Clin. Lab. Standards. 2002. Reference Method for Broth Dilution Anti-fungal Susceptibility Testing of Yeasts; Approved Standard, 2nd ed., M27-A2.
Alexander, B.D. et al. J. Clin. Microbiol. 45(3): 698-706, 2007.
Miyazaki, H. et al. Antimicrob. Agents Chemother. 42: 1695-1701, 1998.
Sanglard, D. et al. Antimicrob. Agents Chemother. 43: 2753-2765, 1999.
Vermitsky, J.-P. et al. Antimicrob. Agents Chemother. 48(10): 3773-3781, 2004.
Kofla, G. et al. J. Microbiol. Methods. 68: 178-183, 2007.
Park, S. et al. Microbiol. Drug Resist. 11(3): 232-238, 2005.
Sambrook et al. Molecular Cloning: A Laboratory Manual, 2nd ed., 1989.
Gait, M.J. Oligonucleotide Synthesis, 1984.
Ausubel, F.M. et al. Current Protocols in Molecular Biology, 1987.
Mullis et al. PCR: The Polymerase Chain Reaction, 1994.
Lamping, E. et al. Eukaryotic Cell, 6(7): 1150-1165, 2007.

* cited by examiner

*Primary Examiner* — Suryaprabha Chunduru
(74) *Attorney, Agent, or Firm* — Siu K. Lo

(57) ABSTRACT

There is disclosed a method for determining azole resistance in *Candida glabrata*. A biological sample containing *Candida glabrata* is obtained and a normalized mRNA level of CDR1 gene is determined using qRT-PCR. Using a microbroth dilution assay conducted at azole concentrations of about 2-8 µg/mL, a susceptible isolate of *Candida glabrata* is obtained. A qRT-PCR assay is employed on the susceptible isolate and an average mRNA level of CDR1 is obtained. A fold-change value for CDR1 is obtained by comparing the CDR1 mRNA level of the biological sample with that of the average mRNA level. A $\geq 2$-fold change value is indicative of an azole resistance in *Candida glabrata*. The present method provides a qRT-PCR assay for azole resistance that has a sensitivity of $\geq 90\%$ and a specificity of $\geq 90\%$.

17 Claims, 9 Drawing Sheets

SEQUENCE LISTING

<160> NUMBER OF SEQ ID NOS: 12

<210> SEQ ID NO 1
<211> LENGTH: 24

```
<212> TYPE: DNA
<213> ORGANISM: Candida glabrata

<400> SEQUENCE: 1
ttaaaagttc aagccagtat ttcc                                    24

<210> SEQ ID NO 2
<211> LENGTH: 24
<212> TYPE: DNA
<213> ORGANISM: Candida glabrata

<400> SEQUENCE: 2
aaatttgata accatcgtaa agca                                    24

<210> SEQ ID NO 3
<211> LENGTH: 23
<212> TYPE: DNA
<213> ORGANISM: Candida glabrata

<400> SEQUENCE: 3
cgctgctgct actgtggcta tct                                     23

<210> SEQ ID NO 4
<211> LENGTH: 22
<212> TYPE: DNA
<213> ORGANISM: Candida glabrata

<400> SEQUENCE: 4
cgctttggac ttcgaacaag aa                                      22

<210> SEQ ID NO 5
<211> LENGTH: 23
<212> TYPE: DNA
<213> ORGANISM: Candida glabrata

<400> SEQUENCE: 5
gttaccgatg gtgatgactt gac                                     23

<210> SEQ ID NO 6
<211> LENGTH: 24
<212> TYPE: DNA
<213> ORGANISM: Candida glabrata

<400> SEQUENCE: 6
aaccgctgct caatcttcct ccat                                    24

<210> SEQ ID NO 7
<211> LENGTH: 24
<212> TYPE: DNA
<213> ORGANISM: Candida glabrata

<400> SEQUENCE: 7
tacatggaac atctgttgct tctt                                    24

<210> SEQ ID NO 8
<211> LENGTH: 20
<212> TYPE: DNA
<213> ORGANISM: Candida glabrata

<400> SEQUENCE: 8
cgactcttca tagccgacgt                                         20

<210> SEQ ID NO 9
<211> LENGTH: 23
```

```
<212> TYPE: DNA
<213> ORGANISM: Candida glabrata

<400> SEQUENCE: 9
gaagaacagc ttgctctcga cga                                              23

<210> SEQ ID NO 10
<211> LENGTH: 20
<212> TYPE: DNA
<213> ORGANISM: Candida glabrata

<400> SEQUENCE: 10
cagacccggt tccggttgta                                                  20

<210> SEQ ID NO 11
<211> LENGTH: 23
<212> TYPE: DNA
<213> ORGANISM: Candida glabrata

<400> SEQUENCE: 11
cggtagtgct tcttgatctc gtt                                              23

<210> SEQ ID NO 12
<211> LENGTH: 24
<212> TYPE: DNA
<213> ORGANISM: Candida glabrata

<400> SEQUENCE: 12
acgctgctga agtccatctc ctcg                                             24
```

METHOD FOR DETERMINING AZOLE RESISTANCE IN CANDIDA GLABRATA

CROSS-REFERENCE TO RELATED APPLICATION

This application claims the priority to U.S. Provisional Application Ser. No. 61/069,105, filed Mar. 12, 2008, the content of which is hereby incorporated by reference in its entirety.

FIELD OF THE INVENTION

The present invention relates generally to the field of diagnosis for anti-microbial resistance in yeast. More specifically, the present invention relates to a method of determining azole resistance in Candida glabrata.

BACKGROUND OF THE INVENTION

Fungal infection in the U.S. has increased significantly over the past three decades, especially among non-albicans species. While Candida albicans remains the primary species involved in Candida infections (40-70%), Candida glabrata is now recognized as the second most common cause (10-30%) and a true emerging pathogen (Ostrosky-Zeichner, L. et al. Antimicrob. Agents Chemother. 47:3149-3154, 2003). Like Candida albicans, Candida glabrata infections can occur in the oral and vaginal mucosal membranes, as well as the urinary tract, and often lead to life-threatening systemic and deep-seated infection within the immuno-compromised host. With its mortality rates up to 51%, the highest amongst the Candida species, Candida glabrata presents a serious threat to immuno-compromised patients (Komshian, S. V. et al. Rev. Infect. Dis. 11:379-390, 1989).

A common fungal infection in healthy women is vulvovaginal candidiasis (WC), which occurs in approximately 75% of women at least once in their lifetime, with 5 to 8% of those individuals developing a recurrent infection (Fidel, P. L. et al. Clin. Microbiol. Rev. 9:335-348, 1996). The epidemiological data on Candida species distribution involved in WC is limited; however, some studies report that Candida albicans accounts for 70-90% of all cases with a recent emergence in non-albicans species being observed. A recent study looking at a large collection of samples from women suspected of having WC found that non-albican species, particularly Candida glabrata, become more prevalent with an increase in age occurring around the time of menopause (Vermitsky, J.-P. et al. J. Clin. Microbiol., 2008). Candida glabrata is the primary non-albicans species emerging in WC, accounting for up to 14% of infections in immuno-competent women and the primary species isolated from diabetic patients (61.3%) and the elderly (51.2%). Several proposed factors may contribute to the emergence of non-albicans species, including the use of azole anti-fungals (e.g., both triazoles and over-the-counter imidazoles), changes in the patient's immune or physiological status, and an increase in the use of chemotherapeutic treatments.

Identifying the species and the antimicrobial susceptibility of an isolate involved in infection is imperative for determining the proper course of treatment. Surveillance programs performed over the past few decades have demonstrated that although azole resistance is rare in Candida albicans isolates (<1%), it is becoming very common among Candida glabrata (up to 15%) and other non-albicans species (Richter, S. S. et al., J. Clin. Micobiol. 45(5):2155-2162, 2005). Current practices for determining the susceptibility of a particular isolate involve the microbroth dilution assay (MBD) outlined by the Clinical Laboratory Standards Institute's (CLSI) M27-2A document (National Committee for Clinical Laboratory Standards. 2002. Reference method for broth dilution antifungal susceptibility testing of yeasts; approved standard, 2nd ed., M27-A2. National Committee for Clinical Laboratory Standards, Wayne, Pa.) as well as several commercially available tests such as Sensititre® YeastOne (Trek Diagnostic Systems, Inc., Westlake, Ohio) and Etest® (AB BIODISK, Solna, Sweden). Although the MBD assay is quite effective, results can take upwards of a week to obtain. Additionally, for Candida glabrata, it was reported that upon comparison with the MBD, these commercially available tests could provide inaccurate or non-concordant susceptibility results, especially when testing with azole anti-fungals (Alexander, B. D. et al., J. Clin. Microbiol. 45(3):698-706, 2007). The need to develop a more rapid, yet still reliable, method for determining the susceptibility of yeast isolates is warranted.

A number of publications have shown that the predominant mechanism of azole resistance in Candida glabrata is the increased constitutive expression of their drug efflux pumps or multidrug resistance genes (MDR) (Miyazaki, H. et al., Antimicrob. Agents Chemother. 42:1695-1701, 1998; Sanglard, D. et al., Antimicrob. Agents Chemother. 43:2753-2765, 1999; Vermitsky, J.-P. et al., Antimicrob. Agents Chemother. 48(10):3773-3781, 2004). Recent publications have established qRT-PCR markers to test for azole resistance in Candida albicans (Kofla, G. et al., J. Microbiol. Methods. 68:178-183, 2007; Park, S. et al., Microbial. Drug Resist. 11(3):232-238, 2005). Due to the fact that resistance is far more prevalent in Candida glabrata than Candida albicans, this organism warrants greater attention when determining a treatment strategy. Moreover, Candida glabrata has the ability to develop frank resistance, which too often results in ineffective azole treatment on resistant (R) or susceptible dose-dependent (S-DD) Candida glabrata isolates and further necessitates azole susceptibility testing. The use of PCR-based identification of molecular markers for susceptibility testing can lead to a more rapid turn-around-time, allowing the physician to choose the proper course of treatment in a timely manner to improve patient outcome. The results of the qRT-PCR assay demonstrate differential expression of MDR genes within S-DD and resistant isolates suggesting different mechanisms between the two susceptibility states.

Despite these known gene expression patterns, though, an effective anti-fungal susceptibility assay with desirable sensitivity and specificity has not yet been described. Investigating this problem, the present inventors found that mere knowledge of the differential expression pattern was insufficient to provide such an assay. Assays that simply categorize isolates as resistant or susceptible based on conventional techniques and calculations often produce false positives and false negatives, each of which presents serious concerns for health care providers and public health officials. The basis for this failure in translating the knowledge into a useful and reliable test for years is unknown.

Accordingly, there is a continuing need for a reliable susceptibility assay for Candida glabrata that offers results in a relatively shorter time frame and high specificity and sensitivity. An improved assay would assist greatly in the detection of azole resistance in Candida glabrata infections from clinical samples, enabling health care providers to initiate proper treatment earlier in the course of the Candida infection.

SUMMARY OF THE INVENTION

The present invention provides a reliable assay for determining azole resistance for Canadida glabrata. Specifically, the present invention is directed to measuring the upregulation of relative mRNA levels of the ABC transporter drug efflux pump (i.e., CDR1) involved in azole resistance by qRT-PCR using primers and dual-labeled probes.

In one aspect, the present invention provides a method for determining azole resistance in *Candida glabrata*, comprising the steps of:
  a) obtaining a biological sample containing *Candida glabrata*;
  b) isolating RNA from said biological sample;
  c) performing qRT-PCR to determine mRNA level of CDR1 gene of said biological sample; and
  d) comparing said mRNA level in step (c) with an average mRNA level to obtain a fold-change value, said average mRNA level is obtained by a process, said process comprises the steps of:
     (i) obtaining an azole susceptible isolate of *Candida glabrata*, wherein said azole susceptible isolate is determined using a microbroth dilution assay conducted at a plurality of azole concentrations of between about 2 µg/mL to about 8 µg/mL;
     (ii) performing qRT-PCR to determine mRNA level of CDR1 gene of said azole susceptible isolate;
     (iii) generating a trend line between normalized CDR1 expression level in step (ii) and said azole concentrations in step (i);
     (iv) calculating the mean of at least one normalized CDR1 expression level above said trend line and at least one normalized CDR1 expression level below said trend line to obtain an average normalized CDR1 expression level for each azole concentration; and
     (v) calculating the mean of said average normalized CDR1 expression levels to obtain said average mRNA level,
  wherein a $\geq$2-fold change value is indicative of azole resistance of said *Candida glabrata* present in said biological sample, and
  wherein said method having a sensitivity of $\geq$90% and a specificity $\geq$90%.

In another aspect, the present invention provides a biological sample that is obtained from a cervicovaginal swab, blood, or urine. Preferably, the biological sample is a cervicovaginal swab.

In another aspect, the present invention provides a RNA isolating step that is performed using guanidine thiocyanate or guanidine hydrochloride.

In another aspect, the present invention provides a qRT-PCR that is TaqMan qRT-PCR or multiplex qRT-PCR.

In another aspect, qRT-PCR uses a forward primer and a reverse primer against CDR1 gene. The forward primer has a nucleotide sequence set forth in SEQ ID NO: 1. The reverse primer has a nucleotide sequence set forth in SEQ ID NO: 2. The qRT-PCR may further comprise a probe, said probe has a nucleotide sequence set forth in SEQ ID NO: 3. Preferably, the probe is dual labeled (FAM-5' TGMGAACAGCT-TGCTCTCGACGA 3'-TAMSp).

In another aspect, the present invention provides an assay for determining azole resistance. Preferably, the azole is triazole. Preferably, the triazole is fluconazole, voriconazole, posaconazole or itraconazole.

In one aspect, the present invention provides a microbroth dilution assay that is conducted at three azole concentrations. Preferably, the azole concentration includes about 2, 4 and 8 µg/mL of fluconazole.

In one aspect, the present invention provides qRT-PCR that employs actin as a reference gene in normalizing CDR1 mRNA.

In one aspect, the present method provides a qRT-PCR assay (for azole resistance in *Candida glabrata* in a biological sample) that reveals a $\geq$2-fold change and a sensitivity of $\geq$90% and a specificity of $\geq$90%.

In one aspect, the present method provides a qRT-PCR assay (for azole resistance in *Candida glabrata* in a biological sample) that reveals a $\geq$3-fold change and a sensitivity of $\geq$95% and a specificity of $\geq$95%.

In yet another aspect, the present invention provides a method for determining azole resistance in *Candida glabrata*, comprising the steps of: a) obtaining a biological sample containing *Candida glabrata*; b) isolating RNA from said biological sample; c) performing qRT-PCR to determine mRNA level of CDR1 gene of said biological sample; and d) comparing the mRNA level of CDR1 from said sample with an average mRNA level obtained from a process employing an azole susceptible isolate of *Candida glabrata*.

In yet another aspect, the present invention provides a method of calculating an average mRNA for CDR1 gene in an azole susceptible isolate, comprising the steps of: (a) obtaining an azole susceptible isolate of *Candida glabrata*, wherein said azole susceptible isolate is determined using a microbroth dilution assay conducted at fluconazole concentrations of 2 µg/mL, 4 µg/mL, and 8 µg/mL; (b) performing qRT-PCR to determine mRNA level of CDR1 gene of the azole susceptible isolate; (c) generating a trend line between normalized CDR1 expression level and the azole concentrations; and (d) calculating the mean of the average normalized CDR1 expression levels to obtain an average mRNA level.

In yet another aspect, the present invention provides a method of comparing the CDR1 mRNA level in a biological sample with an average mRNA level obtained from an azole susceptible isolate to obtain a fold-change value. A $\geq$2-fold change value is indicative of azole resistance of *Candida glabrata* present in said biological sample, and the present method has a sensitivity of $\geq$90% and a specificity $\geq$90%. A $\geq$3-fold change value is indicative of azole resistance of *Candida glabrata* present in said biological sample, and the present method has a sensitivity of $\geq$95% and a specificity $\geq$95%.

DETAILED DESCRIPTION OF THE INVENTION

Figure 1:
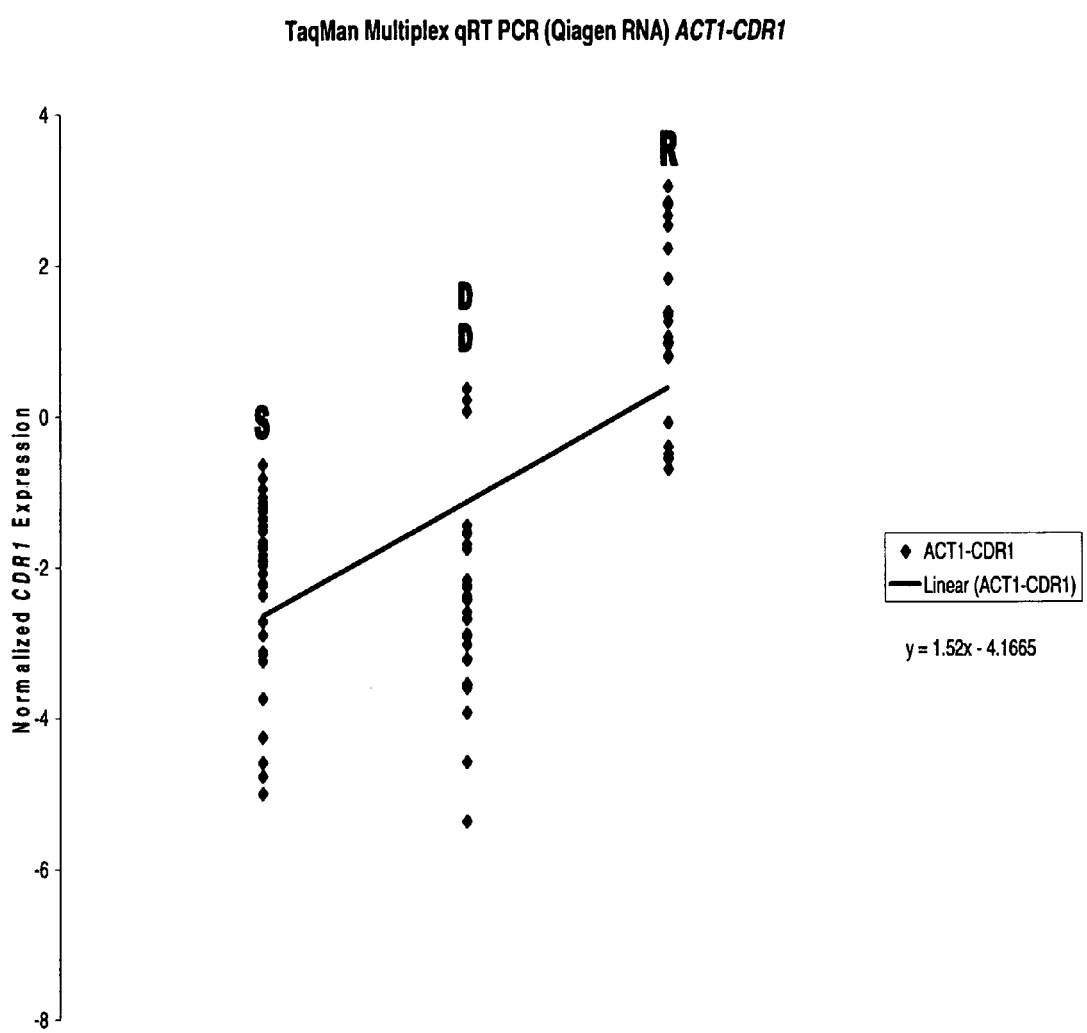
FIG. 1 depicts CDR1 mRNA expression levels for clinical isolates that are categorized as azole susceptible (S), azole susceptible dose dependent (DD), and azole resistant (R) based on the microbroth dilution assay. The line spanning the three data series demonstrates the linear correlation between normalized CDR1 expression and azole resistance. Actin was used as a reference in mRNA normalization.

The following detailed description, including the listed examples and the appended drawings, describes and illustrates various exemplary embodiments of the invention defined by the claims. The description is exemplary in nature and is provided to enable one skilled in the art to practice one or more methods in accordance with the claims.

DEFINITIONS

Various terms used throughout this specification shall have the definitions set out herein.

As used herein, the term "PCR" refers to multiple amplification cycles that selectively amplify a target nucleic acid species. A full description of the PCR process, and common variations thereof, such as real-time qPCR, reverse transcription PCR (RT-PCR) and quantitative reverse transcription PCR (qRT-PCR) are well-described in the art. A typical PCR reaction includes three steps: (i) a denaturing step in which a target nucleic acid is denatured; (ii) an annealing step in which a set of PCR primers (forward and reverse primers) anneal to complementary DNA strands; and (iii) an elongation step in which a thermostable DNA polymerase elongates the primers. By repeating this step multiple times, a DNA fragment is amplified to produce an amplicon, corresponding to the target DNA sequence.

As used herein, the term "qRT-PCR" refers to quantitative reverse transcription polymerase chain reaction. qRT-PCR is used to amplify and simultaneously quantify a targeted RNA molecule. Commonly, the mRNA is converted to complementary DNA (cDNA) through the use of a reverse transcriptase, and the CDNA is then used as a template in a PCR reaction (e.g., real-time PCR). qRT-PCR enables both detection and quantification (as relative amount when normalized to a house-keeping gene such as β-actin) of a specific sequence in a DNA sample such as CDR1.

A "real-time PCR" may use DNA-binding dye to bind to double-stranded (ds)DNA in PCR, causing fluorescence of the dye. An increase in DNA product during PCR therefore leads to an increase in fluorescence intensity and is measured at each cycle, thus allowing DNA concentrations to be quantified. DsDNA dyes such as SYBR Green will bind to all dsDNA PCR products. Fluorescence is detected and measured in the real-time PCR thermocycler, and its geometric increase corresponding to exponential increase of the product is used to determine the threshold cycle ("Ct") in each reaction.

As used herein, the term 'Ct Score' (or "$C_T$" Score) refers to the threshold cycle number, which is the cycle at which PCR amplification has surpassed a threshold level. If there is a higher quantity of mRNA for a particular gene in a sample, it will cross the threshold earlier than a lowly expressed gene since there is more starting RNA to amplify. Therefore, a low Ct score indicates high gene expression in a sample and a high Ct score is indicative of low gene expression.

For purposes of this application, the term "actin" is used interchangeably with the terms "β-actin" or "ACT1."

As used herein, the term "normalized CDR1 expression" refers to Ct score for CDR1 in reference to Ct score for ACT1. For example, Ct score of CDR1 (from qRT-PCR) subtracted from Ct score of ACT1 (from qRT-PCR) (shown in FIG. 4). When calculating fold-change, Ct score of ACT1 (from qRT-PCR) subtracted from Ct score of CDR1 (from qRT-PCR).

As used herein, the term "trend line" refers to a best-fit line connecting the means of normalized CDR1 expressions at various MIC between 2-8 µg/mL fluconazole. Best-fit calculation with the aide of a computer software (e.g., Excel) is known in the art.

As used herein, the term "average mRNA level" refers to the mean of at least one normalized CDR1 expression level above the trend line and at least one normalized CDR1 expression level below the trend line per each MIC concentration between 2-8 µg/mL fluconazole. In one preferred embodiment, the mean of six (6) normalized CDR1 expression levels are used to obtain an average mRNA level at 2, 4 and 8 µg/mL fluconazole.

The practice of the present invention will employ, unless otherwise indicated, various techniques of molecular biology, microbiology, and biochemistry, which are generally within the skill of the art. Such techniques are explained in the literature, such as, "Molecular Cloning: A Laboratory Manual", $2^{nd}$ edition (Sambrook et al., 1989); "Oligonucleotide Synthesis" (M. J. Gait, ed., 1984); "Current Protocols in Molecular Biology" (F. M. Ausubel et al., eds., 1987); and "PCR: The Polymerase Chain Reaction" (Mullis et al., eds., 1994).

As used herein, the term "*Candida glabrata*" refers to a haploid yeast of the genus *Candida*. This species of yeast is non-dimorphic. A major phenotype and potential virulence factor that *Candida glabrata* possesses is low-level intrinsic resistance to the azole drugs, including fluconazole and ketoconazole. This species is still highly vulnerable to polyene drugs such as amphotericin B and nystatin, along with variable vulnerability to flucytosine and caspofungin.

As used herein, the terms "anti-fungal drug" refer to a compound used in the treatment of fungal infection. It includes fungicidal as well as fungistatic compounds, acting either in vitro or in vivo. Examples of anti-fungal compounds include amphotericin B, nystatin, fluconazole, itraconazole, naftifine, ketoconazole, 5-fluorocytosine and griseofulvin. The anti-fungals of the present invention are not limited to any particular mechanism of action.

As used herein, the term "azole resistance" refers to the circumstance when a fungus such as *Candida glabrata* that possesses the ability to grow and maintain viability upon azole drug treatment such as fluconazole and ketoconazole. In this case, these anti-fungal drugs are not effective up to ~30% of cases against *Candida glabrata*. Azole resistance can be either intrinsic or acquired. "Multi-drug resistance" (MDR) means a specific type of drug resistance characterized by cross-resistance of a microorganism to more than one functionally and structurally unrelated drugs. The term "ABC transporter-mediated multi-drug resistance" refers to multi-drug resistance due to the activity of an ABC drug transporter protein (e.g., CDR1).

For purposes of this application, "MDR" genes include at least CDR1, PHD1, PDR1. Both of the CDR1 and PDH1 genes encode ABC transporters that are believed to play a role in multi-drug resistance. CDR1 and PDH1 gene sequences are known in the art. Gene ID Nos. for CDR1 is 2891191 (NCBI) (also, CAGLOM01660g) and PDH1 is 2887804 (NCBI) (also, CAGLOF02717g). PDR1 is a transcriptional factor that is believed to regulate the ABC transporter, including CDR1 and PDH1. Gene ID No. for PDR1 is 2886430 (NCBI) (also, CAGLOA00451g).

As used herein, the term "susceptible" ("S"), when used in connection with *Candida glabrata*, refers to a clinical isolate of this microorganism that exhibits a MIC cutoff of $\leq 8$ μg/mL fluconazole or $\leq 1$ μg/mL voriconazole (in a microbroth dilution assay). A susceptible isolate of *Candida glabrata* refers to an isolate whose growth is inhibited upon azole treatment, leading to a successful patient outcome.

As used herein, the term "susceptible dose-dependent" susceptible" ("S-DD"), when used in connection with *Candida glabrata*, refers to a clinical isolate of this microorganism that exhibits a MIC cutoff of 16-32 μg/mL fluconazole or 2 μg/mL voriconazole (in a microbroth dilution assay). The term "S-DD" and "DD" are used interchangeably. A susceptible dose-dependent isolate of *Candida glabrata* refers to a *Candida glabrata* isolate in a patient whose successful treatment outcome may be achieved at a higher azole dosage (e.g., 800 mg/kg) as compared to that of a standard dosage (i.e., 200-400 mg/kg).

As used herein the term "resistant" ("R"), when used in connection with *Candida glabrata*, refers to a clinical isolate of this microorganism that exhibits a MIC cutoff of $\geq 64$ μg/mL fluconazole or $\geq 4$ μg/mL voriconazole (in a microbroth dilution assay). A resistant isolate of *Candida glabrata* refers to a *Candida glabrata* isolate in a patient who would fail azole treatment even if a high azole dosage (e.g., $\geq 800$ mg/kg) is administered.

As used herein, the term "azole" is a class of five-member nitrogen heterocyclic ring compounds containing at least one other non-carbon atom, nitrogen, sulfur or oxygen.

As used herein, the term "triazole" refers to an azole class containing either one of a pair of isomeric chemical compounds with molecular formula $C_2H_3N_3$, having a five-membered ring of two carbon atoms and three nitrogen atoms. The two isomers include 1,2,3-triazole and 1,2,4-triazole. The triazole anti-fungal drugs include fluconazole, isavuconazole, itraconazole, voriconazole, pramiconazole, and posaconazole.

As used herein, the term "minimum inhibitory concentration (MIC)" refers to the lowest concentration of anti-microbial (e.g., azole) that will inhibit the visible growth of a microorganism (e.g., *Candida glabrata*) after incubation. A MIC is generally regarded as the most basic laboratory measurement of the activity of an anti-microbial agent against a micro-organism. MICs can be determined by a microbroth dilution method usually following the guidelines of a reference body such as the CLSI, BSAC or EUCAST. Clinically, the minimum inhibitory concentrations are used not only to determine the amount of antibiotic that the patient will receive but also the class of antibiotic used, which in turn lowers the opportunity for microbial to develop resistance against specific anti-microbial agents.

As used herein, the term "biological sample" may include but is not limited to blood (e.g., whole blood, blood serum, etc), cervicovaginal swab, urine, cerebrospinal fluid, synovial fluid, and the like from a mammal such as a human or domestic animal. Extraction of nucleic acid (e.g., RNA) from a biological sample is known to one of ordinary skill in the art. The term "clinical isolate" refers to *Candida glabrata* isolated from a biological sample of a subject (such as human).

As used herein, the term "RNA isolation" or "RNA extraction" refers to the purification of RNA from a biological sample. This procedure is complicated by the ubiquitous presence of ribonuclease enzymes in cells and tissues, which can rapidly degrade RNA. Several methods are used in molecular biology to isolate RNA from samples, the most common of these is guanidinium thiocyanate-phenol-chloroform extraction. The method often uses a proprietary formulation of this reagent called Trizol.

In accordance with the present invention, there is disclosed a novel method of determining azole resistance for *Candida glabrata*. The present method is shown to be reliable and has high sensitivity and specificity. The present method has a commercial utility and cures the defects of the prior art methods.

In one embodiment, the present invention provides a method of obtaining an average mRNA level for CDR1 in an azole susceptible *Candida glabrata*, which comprises the steps of: (a) obtaining a clinical isolate of *Candida glabrata* that is azole susceptible, wherein the azole susceptible isolate is determined using a microbroth dilution assay conducted at a plurality of azole concentrations (e.g., fluconazole concentrations of 2 μg/mL, 4 μg/mL, and 8 μg/mL); (b) performing qRT-PCR to determine mRNA level of CDR1 gene of the azole susceptible isolate; (c) generating a trend line between normalized CDR1 expression level and the azole concentrations; and (d) calculating the mean of the average normalized CDR1 expression levels to obtain an average mRNA level.

In another embodiment, the present invention provides a method for determining azole resistance in *Candida glabrata*, comprising the steps of: (a) obtaining a biological sample containing *Candida glabrata*; (b) isolating RNA from said biological sample; (c) performing qRT-PCR to determine mRNA level of CDR1 gene of the biological sample; and (d) comparing the CDR1 mRNA level in a biological sample with an average mRNA level obtained from an azole susceptible isolate to obtain a fold-change value.

In accordance with the present invention, the qRT-PCR assay provides a $\geq 2$-fold change value that is indicative of azole resistance of *Candida glabrata* present in a biological sample, and the assay has a sensitivity of ≧90% and a specificity ≧90%.

In accordance with the present invention, the qRT-PCR, assay provides a ≧3-fold change value that is indicative of azole resistance of *Candida glabrata* present in a biological sample, and the assay has a sensitivity of ≧95% and a specificity ≧95%.

After a biological sample is obtained from a human subject, the biological sample is streaked onto *Candida* CHROMagar to isolate *Candida glabrata*. *Candida glabrata* cultures are grown in YPD (yeast extract-peptone-dextrose medium) and used to perform microbroth dilution assays to determine azole susceptibility. In one embodiment, the azole susceptibility of a clinical isolate employs a microbroth dilution assay. In determining whether a clinical isolate containing *Candida glabrata* is susceptible ("S"), susceptible dose-dependent ("S-DD") or resistant ("R"), the microbroth dilution assay is conducted at ≦8 µg/mL, 16-32 µg/mL, and ≧64 µg/mL fluconazole. Alternatively, the microbroth dilution assay may be conducted using ≦1 µg/mL, 2 µg/mL, and ≧4 µg/mL voriconazole. Such microbroth dilution assay using these concentrations of fluconazole allow one of skilled artisan to determine whether a clinical isolate is azole susceptible, azole susceptible dose-dependent or azole resistant. In another embodiment, the selected isolates use azole concentrations of about 2, 4, 8, 16, 32, and 64 µg/mL.

In another embodiment, a susceptible clinical isolate is further determined using a micrbroth dilution assay whereby the assay is conducted at a concentration between 2 µg/mL to 8 µg/mL fluconazole. A plurality of fluconazole concentration may be employed in the microbroth dilution assay.

In a preferred embodiment, three (3) doses of azole concentrations may be used. One of ordinary skills in the art would recognize that more doses (e.g., four (4) doses or five (5) doses etc) of azole concentrations may be employed. In a preferred embodiment, a susceptible clinical isolate may be exposed at about 2 µg azole/mL, about 4 µg azole/mL and about 8 µg azole/mL. Fluconazole is a preferred azole. After culture, the RNAs of these susceptible clinical isolates are harvested and qRT-PCT is used to determine the CDR1 mRNA expression levels in these isolates. Actin is used as a reference to provide a relative change in CDR1 mRNA expression.

CDR1 mRNA expression is normalized using ACT1 expression. Multiplex qRT-PCR permits the simultaneous determination of CDR1 mRNA as well as actin mRNA so that one of skilled artisan would use these mRNA values for normalization. Alternatively, separate qRT-PCR reactions may be performed. The normalized CDR1 mRNA expression of each isolate is plotted on the y-axis against increasing MIC on the x-axis to create a scatter plot.

An average of the normalized CDR1 expression values for each MIC concentration is calculated. The average normalized CDR1 values are connected to create a trend line, using a best-fit line. The trend line indicates a slope upward, evidencing that CDR1 expression is correlated with an increased MIC concentration (between 2-8 µg/mL fluconazole) in the azole susceptible isolate. Once the trend line is established, at least two (2) isolates from each fluconazole dose are chosen as representatives for that MIC value. Preferably, one (1) isolate is chosen from above the trend line. Another one (1) isolate is chosen from below the trend line. An average of normalized CDR1 values from these two isolates is obtained to calculate an approximation of the mean. Similar calculation is performed at a different MIC value in order to obtain a second approximation of the mean for that particular MIC. The average of the mean approximations is then calculated (i.e., average mRNA level), which is then used as a baseline for calculating a fold-change when compared to CDR1 mRNA level determined by qRT-PCR from a biological sample. In one embodiment, the average of six (6) isolates (two (2) from MIC values of 2, 4, and 8 µg/mL fluconazole) will be used to establish a baseline for susceptible CDR1 expression, from which fold-changes can be calculated.

In accordance with the invention, an average mRNA level may be determined using ~30 azole susceptible clinical isolates. In order to obtain these numbers of isolates, it is estimated that ~100 biological samples are required for microbroth dilution assay. It is estimated that ~30% of the 100 of *Candida glabrata* samples are susceptible to fluconazole (MIC ≦8 µg/mL) (See, Table 1).

In one embodiment, the azole susceptible group has thirty (30) azole susceptible isolates as determined by a microbroth dilution assay. These azole susceptible isolates contains five (5) isolates at the MIC of 2 µg/mL fluconazole, twenty one (21) isolates at the MIC of 4 µg/mL fluconazole and four (4) isolates at the MIC of 8 µg/mL fluconazole.

One of ordinary skill in the art would recognize that more isolates may be used per each MIC doses. For example, four (4) isolates from each MIC dose may be used to calculate the average normalized CDR1 expression. Without wishing to be bound by a theory, the number of isolates may be optimized by one skilled in the art to obtain an optimal value.

In order to determine the average mRNA level of the CDR1 gene, the present inventors found that at least two azole isolates identified as susceptible by the microbroth dilution assay should be used. mRNA expression may be determined by qRT-PCR. Preferably, the mRNA expression is determined by conventional RT-PCR, qRT-PCR, or multiplex qRT-PCR.

In one embodiment, RNA from a biological sample or clinical isolate may be isolated standard protocols that are known to one of ordinary skill in the art, including guanidine thiocyanate and guanidine hydrochloride. In one embodiment, the biological sample is obtained from a cervicovaginal swab, blood, or urine.

Primers for PCR amplification of target sequences (e.g., mRNA sequences of CDR1 gene) can be designed based on the sequence of the target sequence, in accordance with standard procedures. Design and synthesis of such primers is well within the abilities of those of skill in the art. Primers function to anneal and amplify a unique target sequence and as a generator of a signal for detection and monitoring of an amplification reaction. Thus, in some embodiments, the primers are unlabeled (such as in conventional PCR). While in other embodiments, the primers are labeled, such as with a fluorescent moiety. Labeled primers can be of any type, including those that are typically used in qRT-PCR reactions, such as Scorpions, Molecular Beacons, and the like.

Probes may be provided in addition to primers. Probes that can be used for detection of amplification of the unique genomic sequences (e.g., TaqMan™ probes) can be designed to hybridize to a sequence between the two amplification primers, preferably within 5-15 bases of one of the primer binding sites. Design and synthesis of such probes is well within the abilities of those of skill in the art. Typically, probes are present in reaction mixtures in conjunction with primers or sets of primers for a particular amplification reaction, whether it be an amplification of a unique target sequence. However, probes may be provided as separate components, which are separate from the primer(s) or other components of a reaction mixture.

The primers and probes are designed to have the typical size for primers and probes for use in PCR reactions. In general, the primers are relatively short (about 10-30 bases in length) oligonucleotides, while the probes (e.g., TaqMan® probes) may be from about 15-35 bases in length. The primers and probes are designed through a process that includes identification of unique sequences on a target nucleic acid, designing short oligonucleotides to amplify or detect those sequences, and synthesizing the oligonucleotides. Several characteristics may be taken into consideration when designing the primers and probe: e.g., the probe melting temperature should be higher than the primer melting temperatures, and the distance between the 3'-end of one primer and the 5'-end of the probe may be greater than 8 nucleotides. One of skill in the art is well aware of these considerations and characteristics, and may select among them to provide suitable primers and probes according to the invention without undue or excessive experimentation. Protocols for synthesis of oligonucleotides are known to those skilled in the art. Any suitable protocol may be used in synthesizing the primers and probes of the invention.

Within context of the present invention, precise sequence of a particular primer is not critical. Primers according to the invention are typically used in pairs to amplify unique genomic sequences such as CDR1 or ACT1. Thus, according to an embodiment of the invention, primer pairs that function to amplify the target gene is suitable for use in the invention. Primer pairs may be devised by those of skill in the art without undue experimentation, now that the genomic sequence for MDR genes (i.e., CDR1, PDH1 and PDR1) in *Candida glabrata* is known. The concept of the invention may be applied to any primers that are specific for these unique genomic sequences.

In an exemplary embodiment, the forward primer for CDR1 having a nucleotide sequence set forth in SEQ ID NO: 1. The reverse primer CDR1 having a nucleotide sequence set forth in SEQ ID NO: 2. The molecular probe for CDR1 has a nucleotide sequence set forth in SEQ ID NO: 3. In another exemplary embodiment, The forward primer for ACT1 having a nucleotide sequence set forth in SEQ ID NO: 4. The reverse primer ACT1 having a nucleotide sequence set forth in SEQ ID NO: 5. The molecular probe for ACT1 has a nucleotide sequence set forth in SEQ ID NO: 6.

Given the genomic sequence for the MDR genes is available, one of skilled in the art would recognize that equivalent primers may be designed and used employing the present method. The qRT-PCR for amplifying CDR1, PDH1, and PDR1 genes is not primer-specific. Other equivalent primers and probes may be prepared to achieve the same qRT-PCR amplification results (compared to the exemplary primers disclosed herein). The design and preparation of these equivalent primers are within the skilled in the art's knowledge. Accordingly, the present invention is intended to encompass all equivalent primers insofar as they could be used in the qRT-PCR method.

According to the invention, actin is used as the normalizer for the relative quantification of mRNA expression for CDR1. In order to compare the gene expression level in two or more biological samples, the actin is used as an internal normalizer. Other housekeeping genes (e.g., GAPDH) may also be used. The Ct values obtained from qRT-PCR reaction can be used for the normalization of Ct values obtained from actin.

In exemplary embodiments of the present invention, PCR primers have been designed and synthesized to amplify the CDR1 and actin sequences. Running this control qRT-PCR actin reaction simultaneously with qRT-PCR (either in the one or two tube reaction format) allows normalizing of the amount of nucleic acid (e.g., CDR1) being amplified. The normalized CDR1 levels among different biological samples provide a qualitative comparison of two or more biological samples for their CDR1 expression.

Quantitative real-time RT-PCR is an accurate, precise, high throughput assay. Real-time PCR automates the process of quantitating reaction products for each sample in every cycle. In some embodiments, real-time PCR systems rely upon the detection and quantitation of a fluorescent reporter, the signal of which increases in direct proportion to the amount of PCR product in a reaction. In the simplest and most economical format, that reporter is the double-stranded DNA-specific dye SYBR® Green (Molecular Probes). SYBR Green binds double-stranded DNA, and upon excitation emits light. Thus, as a PCR product accumulates, fluorescence increases.

The SYBR® Green (Molecular Probes, Eugene, Oreg.) system is a simple and cost-effective way to detect and quantitate PCR products in real time. The SYBR® Green dye binds, in a sequence non-specific manner, to double-stranded nucleic acids. It thus can be used for detection and quantitation of double-stranded products produced from single-stranded templates (e.g., mRNA). Other detectable probes and primers, such as Sunrise™ primers, amplifluor probes, and DNAzymes, mat be optimized to be used for quantitative detection of amplification products.

Two alternatives to SYBR Green are TaqMan® (Applied Biosystems, Foster City, Calif.) and molecular beacons, both of which are hybridization probes relying on fluorescence resonance energy transfer (FRET) for quantitation. TaqMan Probes are oligonucleotides that contain a fluorescent dye, typically on the 5' base, and a quenching dye, typically located on the 3' base. More specifically, for TaqMan® probes, when the probe is intact, the quencher quenches the signal produced by the fluorescent label. However, upon binding of the probe to the target sequence and subsequent digestion of the probe by the 5'-3' exonuclease activity of a polymerase, such as Taq polymerase, the fluorescent moiety is released from the quencher moiety, and a detectable signal, which is proportional to the amount of target nucleic acid being produced, is produced and can be monitored. In one embodiment, Taq polymerase are used in qRT-PCR due to its 5'-3' exonuclease activity and it changes the fluorescence of the probes and allows amplification of CDR1 mRNA. TaqMan® probes rely on degradation by a polymerase to generate a detectable signal, whilst Scorpions and Molecular Beacons rely on opening of a hairpin structure to provide a detectable signal. Like TaqMan® probes, Scorpion probes contain both a fluorescent moiety and quenching moiety on a single probe. However, unlike TaqMan® probes, Scorpions are not degraded during the amplification reaction. Rather, they are designed as primers for amplification reactions. Scorpion primers are designed to form hairpin structures in solution, which causes the fluorescent moiety and the quenching moiety to be in close proximity. Binding of the primers to target nucleic acids unfolds the hairpin structure and moves the quenching moiety a sufficient distance away from the fluorescent moiety that detectable fluorescence is emitted.

In one embodiment, the present invention provides a method of using TaqMan qRT-PCR. TaqMan probes may be used with Quanta's OneStep qRT PCR buffer. TaqMan probes only fluoresce when the target sequence of the probe is amplified by the qRT PCR. The probe, consisting of a reporter dye and quencher, binds a target sequence and is subsequently cleaved by DNA Polymerase during the extension step of the qRT-PCR, releasing the dye from its quencher and emitting fluorescence. Multiplex TaqMan qRT-PCR also uses ACT1 as a normalizer. This method produced high sensitivity and specificity levels acceptable in a clinical setting.

Molecular beacons also contain fluorescent and quenching dyes, but FRET only occurs when the quenching dye is directly adjacent to the fluorescent dye. Molecular beacons are designed to adopt a hairpin structure while free in solution, bringing the fluorescent dye and quencher in close proximity. When a molecular beacon hybridizes to a target, the fluorescent dye and quencher are separated, FRET does not occur, and the fluorescent dye emits light upon irradiation.

In one embodiment, the present invention provides a qRT-PCR assay to quantify the mRNA expression level of CDR1 gene (in order to determine the azole resistance in *Candida glabrata*. Accordingly, quantitation of mRNA transcription levels is important in assessing azole resistance. Real-time qRT-PCR disclosed herein provides a useful means in determining, in real-time, the amount of mRNA of CDR1 in a biological sample. qRT-PCR represents a sensitive method currently available for detecting and quantitating mRNA.

Multiplexing of PCR reactions is common. Multiplexing allows an investigator to assay two or more different gene targets in a single reaction through the use of multiple probes or primers, each specific for its own target and each comprising a fluorescent moiety that emits at a unique wavelength (as compared to the other probes). Multiplexing is possible with TaqMan® probes, Molecular Beacons, and Scorpions. Due to its non-specific binding. nature, SYBR® Green may not be amenable to multiplexing.

In one embodiment, the present invention provides a method of using multiplex qRT-PCR. To account for potential errors due to the quantitation of ACT1 in a different aliquot of RNA than the gene of interest, ACT1 may be quantitated in the same reaction as the gene of interest is conducted using a TaqMan Multiplex qRT-PCR. Extracted RNA is used. This method also produces high sensitivity and specificity levels that are acceptable in a clinical setting.

Typically, a qRT-PCR reaction is performed by one of two methods: comparison to a standard curve or comparison of Ct values. In the first of these methods, a standard curve of amplification products of a particular mRNA is made based on amplification of a series of different, known amounts of a pre-selected nucleic acid. Amplification results of reactions performed on a target nucleic acid are then compared to the standard curve to obtain a quantity, and that quantity can be extrapolated to an amount of the target in the original sample. While it is preferred to use an mRNA as the source for the standard curve, the stability of mRNA is known to affect the validity of such standard curves, and overcoming or minimizing this problem has proved to be difficult. To avoid the problems associated with using mRNA as a source for the standard curve, researchers have used DNA for generation of standard curves. While use of DNA overcomes the problems associated with use of mRNA, the mere fact that it avoids the problems creates yet another problem. That is, because DNA templates are relatively stable, and because amplification of DNA does not require a first-strand synthesis step (which can be inefficient and variable across samples or preparations), the standard curves produced from DNA sources often do not correlate accurately to the amount of mRNA in a test sample.

In the Ct comparison method for quantitating PCR products, expression of a housekeeping gene (such as actin) is used as a standard against which amplification of a target nucleic acid (CDR1) is compared. Often, in this method, a comparison of expression of the target nucleic acid under two different conditions is performed to determine changes in expression patterns. This method avoids the problems associated with instability of RNA or use of DNA as a control that is seen when using the classical standard curve method.

Recently, researchers have attempted to use controls that are amplified in the same PCR reaction mixture as the target sequence in an effort to quantitate PCR products and determine amounts of target nucleic acids in a sample. These controls are often transcripts of house-keeping genes. The control is added to the reaction mix and co-amplified with the target nucleic acid. Fluorescent probes specific for both are included in the mixture, and two amplification curves are obtained. The relative expression of the target nucleic acid with respect to the control is then determined. Using this technique, multiple different samples can be compared for expression of CDR1, with reference back to the same control. Although adding a control to amplification reactions can be a useful alternative to other methods of quantitating expression levels, and can be a useful method for normalizing PCR reactions across samples, it does not allow one to determine absolute amounts of materials present in the amplification reaction mixture or in the original sample. Rather, the results are qualitative or semi-quantitative, giving an idea only of the amount of one nucleic acid (e.g., the target) in comparison to another (e.g., the control).

In exemplary embodiments, the azole is a triazole. In some exemplary embodiments, the azole is fluconazole, voriconazole, posaconazole and itraconazole.

In one embodiment, the present method provides a qRT-PCR assay that has ≧2-fold-change value of CDR1 expression. Such an increase in fold-change is indicative of azole resistance of said *Candida glabrata* present in the biological sample. The assay that exhibits ≧2-fold-change value of CDR1 expression has a sensitivity of ≧90% and a specificity ≧90%.

In another embodiment, the present method provides a qRT-PCR assay that has ≧3-fold-change value of CDR1 expression. Such an increase in fold-change is indicative of azole resistance of said *Candida glabrata* present in the biological sample. The assay that exhibits ≧3-fold-change value of CDR1 expression has a sensitivity of ≧95% and a specificity ≧95%.

In yet another embodiment, the present invention provides a kit. In general, such a kit may contain some or all of the components necessary to practice a method of the invention. Thus, for example, the kit may contain one or more primer (e.g., lyophilized or purified primers) or one or more composition (e.g., stock solution or amplification reaction) of the present invention. Likewise, the kit may contain multiple primers, or sets of primers, for amplification of unique genomic sequences for CDR1 and actin for amplification. In a preferred embodiment, a kit of the invention further comprises a container housing the primer(s) of the present invention, as well as an instruction for performing the PCR steps.

EXPERIMENTAL STUDIES

The invention can be understood more fully by reference to the following illustrative examples, which are intended to exemplify non-limiting embodiments of the invention.

Example 1

Anti-Fungal Susceptibility of Clinical Isolates Containing *Candida glabrata*: Determination By Microbroth Dilution Assay One hundred seventy-five (175) *Candida glabrata* clinical isolates were retrieved from cervicovaginal swabs. Clinical isolates were obtained from cervicovaginal swabs of female patients suspected of having vulvovaginal candidiasis (WC)

from across the United States. *Candida glabrata* PCR positive swabs were struck out on *Candida* CHROMagar, and individual *Candida glabrata* colonies were isolated for susceptibility testing using the microbroth dilution assay according to the Clinical and Laboratory Standards Institute protocol. Susceptibilities of these isolates to triazole anti-fungal drugs (e.g., fluconazole, voriconazole, and miconazole) were determined.

The distribution of these clinical isolates fell into three susceptibility groups with respect to fluconazole and voriconazole MIC breakpoints. For fluconazole, there were 30.9% susceptible (S)($\leq$8 µg/ml), 42.2% susceptible dose-dependent (S-DD)(16-32 µg/ml) and 26.9% resistant (R)($\geq$64 µg/ml) isolates. The number of voriconazole R isolates ($\geq$4 µg/ml; 24%) was comparable to fluconazole. However, a decrease in the number of S-DD isolates (2 µg/ml; 13.7%) and an increase in S isolates ($\leq$1 µg/ml; 62.3%) was observed when compared to fluconazole. All of the clinical isolates were susceptible to miconazole, which is consistent with previous studies of cervicovaginal isolates (See, Table 1).

Example 2

Wide Variation in CDR1 Expression Levels in Azole Susceptible *Candida glabrata* Isolates To identify if a multidrug resistance (MDR) gene may serve as an appropriate molecular marker for determining azole resistance in *Candida glabrata*, we investigated the relationship between increased expression of the MDR genes CDR1, PDH1, PDR1 and an increase in fluconazole minimum inhibitory concentrations.

Using qRT-PCR to monitor CDR1 mRNA expression and actin as reference (i.e., normalized using ACT1 mRNA expression), we observed a wide range of CDR1 expression levels among different isolates that were all identified as azole susceptible *Candida glabrata* isolates based on the microbroth dilution assay (i.e., $\leq$8 µg/mL fluconazole). Raw mRNA expression levels were calculated using the equation: (ACT1 Ct Score—Gene of Interest Ct Score). Upon comparing the raw scores for each of the *Candida glabrata* MDR genes, a correlation between increases in expression of these genes with an increase in fluconazole MIC was investigated.

FIG. 1 shows a wide range of CDR1 mRNA expression in thirty (30) RNA extractions comprised of ten (10) susceptible isolates with three (3) independent RNA extractions for each (See, Table 1, "S"). Clinical isolates were determined to be susceptible based on the microbroth dilution assay.

This unexpected finding has significant implications. The observed wide variation in CDR1 expression might negatively impart the sensitivity and specificity of a molecular-based azole susceptibility assay. A qRT-PCR based azole susceptibility assay often utilizes an expression level of CDR1 in such isolates as a baseline for comparison and, ultimately, for the determination of whether a biological sample includes *Candida glabrata* that is susceptible or resistant to an azole. As shown below, a wide variation of CDR1 expression in azole susceptible isolates renders the qRT-PCR assay unreliable.

Example 3

Linear Correlation Between Increased CDR1 Expression and Increased MIC qRT-PCR was used to determine the CDR1 mRNA expression in all the clinical isolates (composed of susceptible ["S"], susceptible dose-dependent ["DD"] and resistant ["R"] groups). FIG. 1 depicts a strong linear correlation in resistant isolates having considerably higher expression of CDR1 in the S-DD and R groups. This observation is consistent with the notion that CDR1 expression is a good biomarker for azole resistant determination in *Candida glabrata*.

Figure 2:
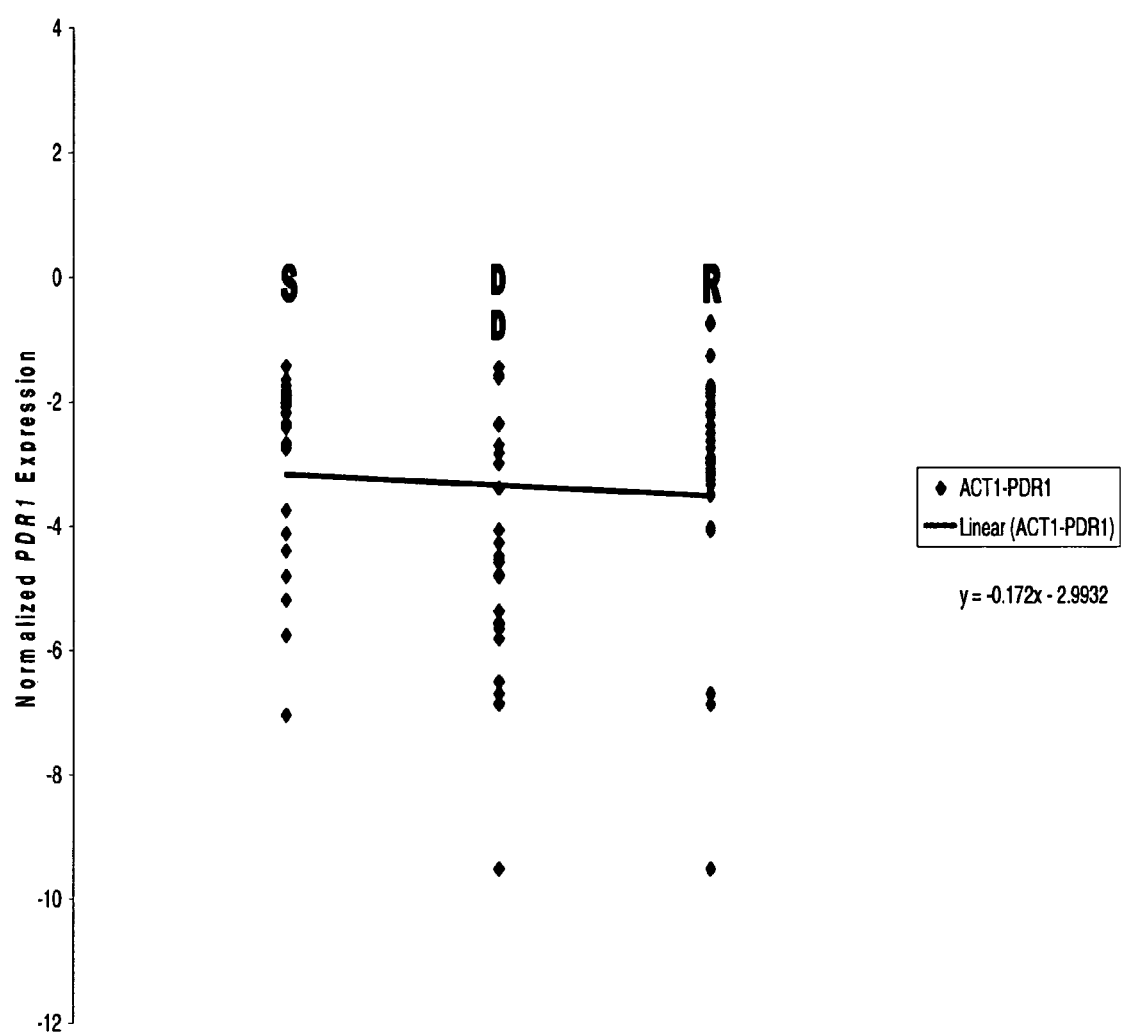
FIG. 2 depicts PDR1 mRNA expression levels for clinical isolates that are categorized as azole susceptible (S), azole susceptible dose dependent (DD), and azole resistant (R) based on the microbroth dilution assay. The line spanning the three data series demonstrates a lack of linear correlation between normalized PDR1 expression and azole resistance. Actin was used as a reference in mRNA normalization.
Figure 3:
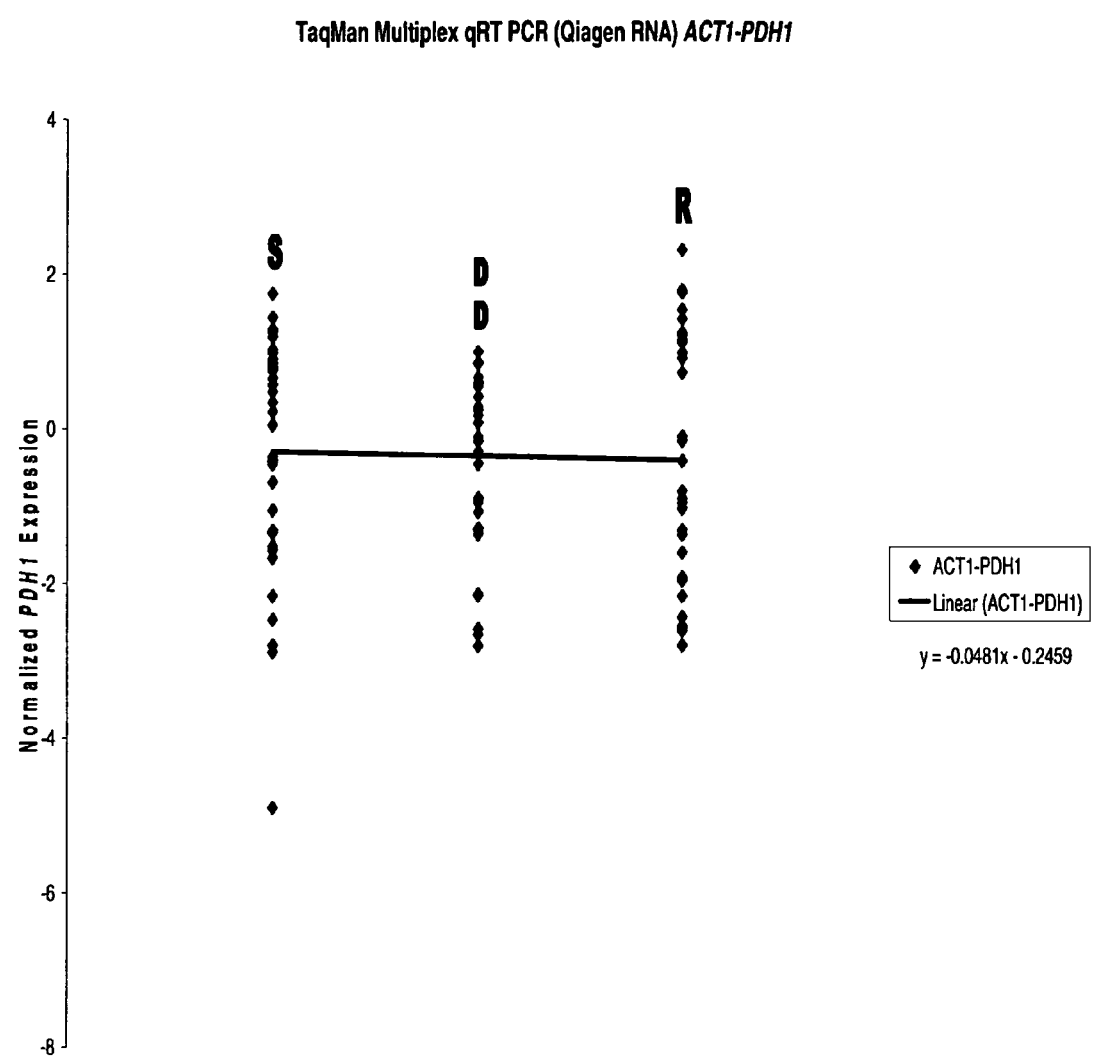
FIG. 3 depicts PDH1 mRNA expression levels for clinical isolates that are categorized as azole susceptible (S), azole susceptible dose dependent (DD), and azole resistant (R) based on the microbroth dilution assay. The line spanning the three data series demonstrates a lack of linear correlation between normalized PDH1 expression and azole resistance. Actin was used as a reference in mRNA normalization.

The correlation between CDR1 mRNA expression and azole susceptibility in clinical isolates is found to be unique. Both PDR1 (See, FIG. 2) and PDH1 (See, FIG. 3) mRNA expression (normalized by ACT1) failed to show any linear correlation, indicating only CDR1 (not PDR1 and PDH1) could serve as a good marker for azole resistant in *Candida glabrata*.

Example 4

Identification of Potential Problems Associated with Wide Variable CDR1 Baseline Inasmuch as CDR1 may be used to determine azole resistant in *Candida glabrata*, the wide CDR1 baseline expression poses serious difficulties in the development of a reliable commercial test whether a particular biological sample included *Candida glabrata* that demonstrated azole resistance. We therefore examined the effects of the wide variation in CDR1 baseline in the susceptible clinical isolates on the overall qRT-PCR assay.

In these studies, we used a random CDR1 mRNA level obtained from one susceptible strain as a baseline. The baseline CDR1 mRNA level is used to compare with those CDR1 mRNA levels obtained from clinical isolates that had been previously determined as azole resistant (according to the golden standard "microbroth dilution assay"). In order to illustrate the potential problems, we arbitrarily chose one high value and one low value in CDR1 mRNA expression in the susceptible clinical isolates as a reference. Using these values as a reference, we sough to determine if they serve as a reliable baseline in azole resistant determination.

(A) Use of A Low CDR1 mRNA Value as Baseline.

Figure 5:
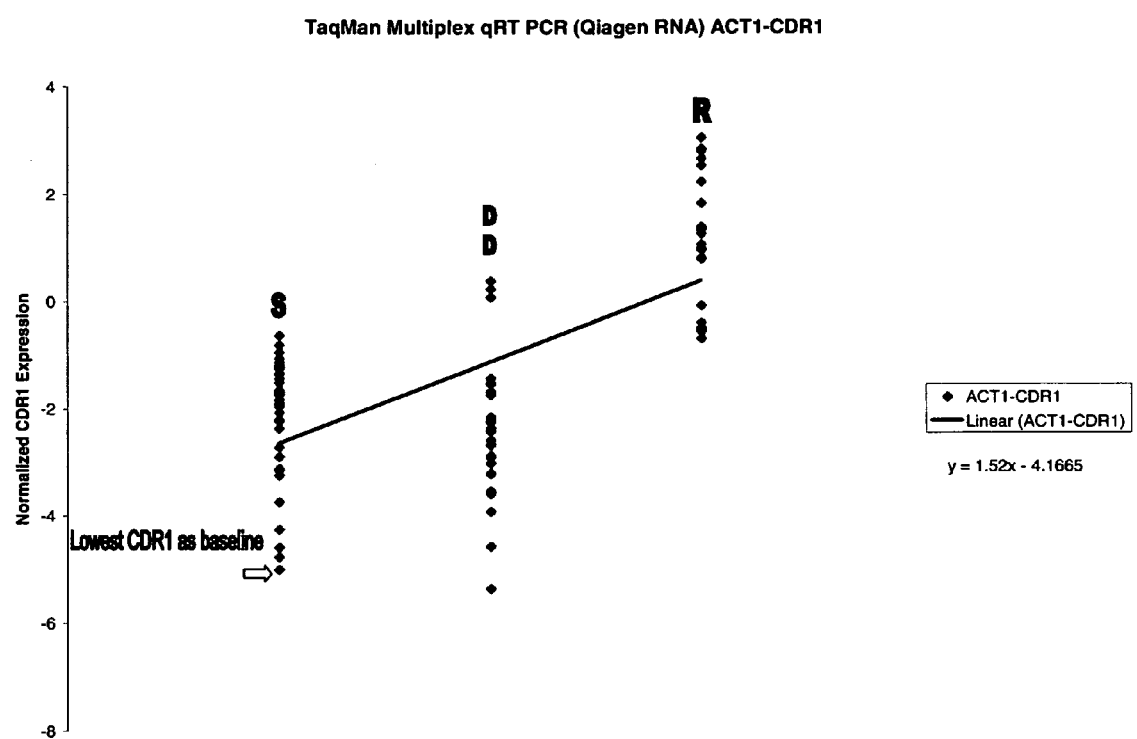
FIG. 5 depicts CDR1 mRNA expression levels for clinical isolates that are categorized as azole susceptible (S), azole susceptible dose dependent (DD), and azole resistant (R) based on the microbroth dilution assay. The line spanning the three data series demonstrates the linear correlation between normalized CDR1 expression and azole resistance. Actin was used as a reference in mRNA normalization. The arrow indicates the lowest normalized CDR1 value (in the S group) and it is used as a baseline for comparing CDR1 mRNA obtained from biological samples (See, Example 4)

FIG. 5 depicts the use a low CDR1 mRNA value (arrowed) as baseline. In this study, we characterized, using a microbroth dilution assay, of thirty (30) clinical isolates containing *Candida glabrata*. As shown in Table 2, the thirty (30) clinical isolates included ten (10) azole resistant ("R") isolates and twenty (20) isolates were azole susceptible ("S") and susceptible-dose dependent ("S-DD").

When a low CDR1 expression level (represented by the arrow in FIG. 5) was chosen as the baseline, the comparison gives twenty (20) azole resistant ("R") and ten (10) azole susceptible and susceptible-dose dependent (when based on the calculated expression level of CDR1 $\geq$2-fold) (Table 2). The assay has a sensitivity of 1.0 and a specificity of 0.5 (Table 2).

The comparison further gives twelve (12) azole resistant and eighteen (18) azole susceptible and susceptible-dose dependent (when based on the calculated expression level of CDR1 $\geq$3-fold), with a sensitivity of 1.0 and a specificity of 0.9 (Table 2).

In sum, these comparisons produced many false positive results and reduced significantly the specificity of the qRT-PCR assay. (Table 2)

(B) Use of A High CDR1 mRNA Value as Baseline

Figure 6:
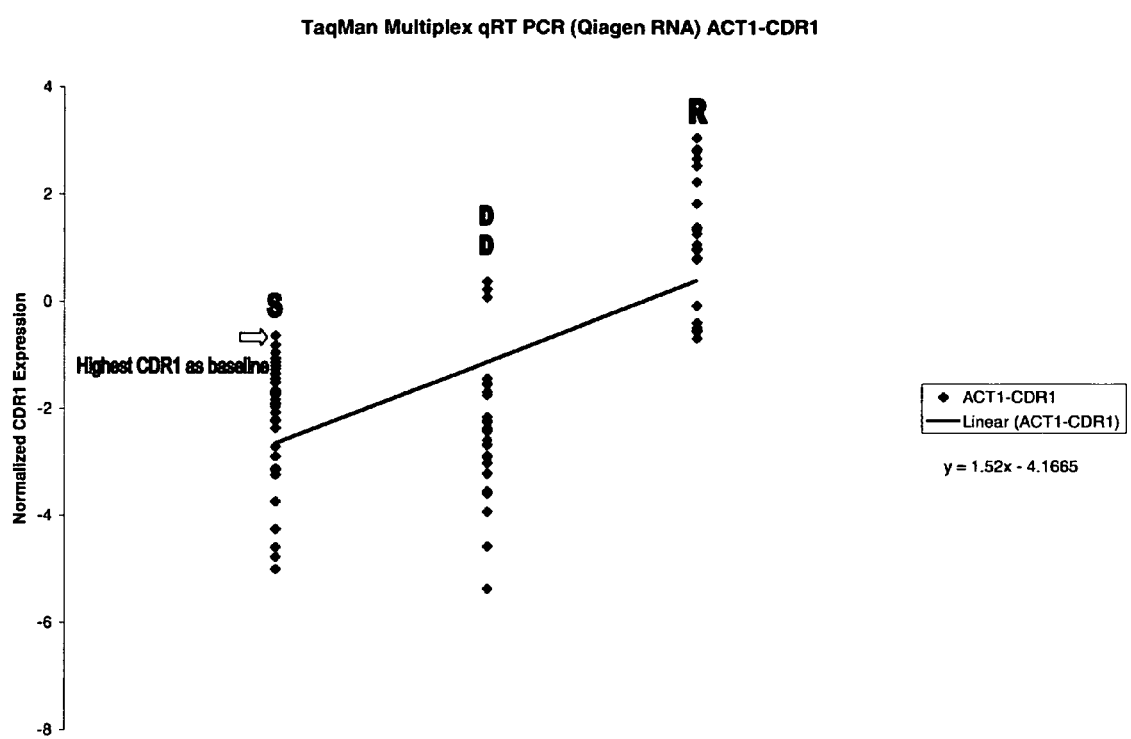
FIG. 6 depicts CDR1 mRNA expression levels for clinical isolates that are categorized as azole susceptible (S), azole susceptible dose dependent (DD), and azole resistant (R) based on the microbroth dilution assay. The line spanning the three data series demonstrates the linear correlation between normalized CDR1 expression and azole resistance. Actin was used as a reference in mRNA normalization. The arrow indicates the highest normalized CDR1 value (in the S group) and it is used as a baseline for comparing CDR1 mRNA obtained from biological samples (See, Example 4).

FIG. 6 depicts the use a high CDR1 mRNA value (arrowed) as baseline. In this study, we used the same thirty (30) clinical isolates that had been characterized in terms of their azole resistant characteristics using a microbroth dilution assay. As shown above, there were 10 azole resistant ("R") and 10 azole susceptible ("S") and susceptible-dose dependent ("S-DD") strains in the 30 clinical isolates examined.

When a high CDR1 expression level (represented by the arrow in FIG. 6) was chosen as the baseline, the comparison gives eight (8) azole resistant ("R") and twenty two (22) azole susceptible ("S") and susceptible-dose dependent ("S-DD") (when based on the calculated expression level of CDR1 ≧ 2-fold) (Table 3). The assay has a sensitivity of 0.8 and a specificity of 1 (Table 2).

The comparison further gives five (5) azole resistant ("R") and twenty five (25) azole susceptible ("S") and susceptible-dose dependent ("S-DD") (when based on the calculated expression level of CDR1 ≧3-fold) (Table 3). The assay has a sensitivity of 0.5 and a specificity of 1.0 (Table 2).

These comparisons produced many false negative results and adversely affected the sensitivity required in a commercial assay that employs qRT-PCR.

Altogether, based on these studies, we concluded that random selection of a CDR1 expression value would not provide a reliable baseline for determining azole resistance. These studies clearly show that using the expression level of CDR1 mRNA from a single isolate, although demonstrated to correlate with an increased azole MIC (e.g., Lamping et al. Eukarvotic Cell, 6(7): 1150-1165. 2007), as a baseline for comparison in a molecular-based azole susceptibility assay would likely lead to false positives or false negatives, both of which would reduce the overall reliability and usefulness of the assay.

To the best of the present inventors' knowledge, there has been no report revealing a wide variation of CDR1 expression in azole susceptible *Candida glabrata*. Because the scientific community is unaware of such wide variation of baseline CDR1 expression in the susceptible isolates, most of the scientific communities use either a single isolate or a single CDR1 expression value. The use of a single CDR1 expression value does not serve as a reliable baseline in qRT-PCR assay when used in determining azole resistant for *Candida glabrata*.

Example 5

Linear Correlation Trend for CDR1 Expression Levels in Azole Susceptible Isolates Upon observing the wide variation in CDR1 expression among susceptible isolates, we further examined if CDR1 expression may change with respect to different doses of azole.

In this series of study, we subdivided the susceptible isolates and exposed them to various doses of azole drugs. Specifically, we cultured susceptible isolates in low, medium, and high susceptible MICs (i.e., 2, 4, and 8 µg/mL fluconazole, respectively). qRT-PCR was used to determine the CDR1 expression was monitored using qRT-PCR and ACT1 was used as a reference.

Figure 4:
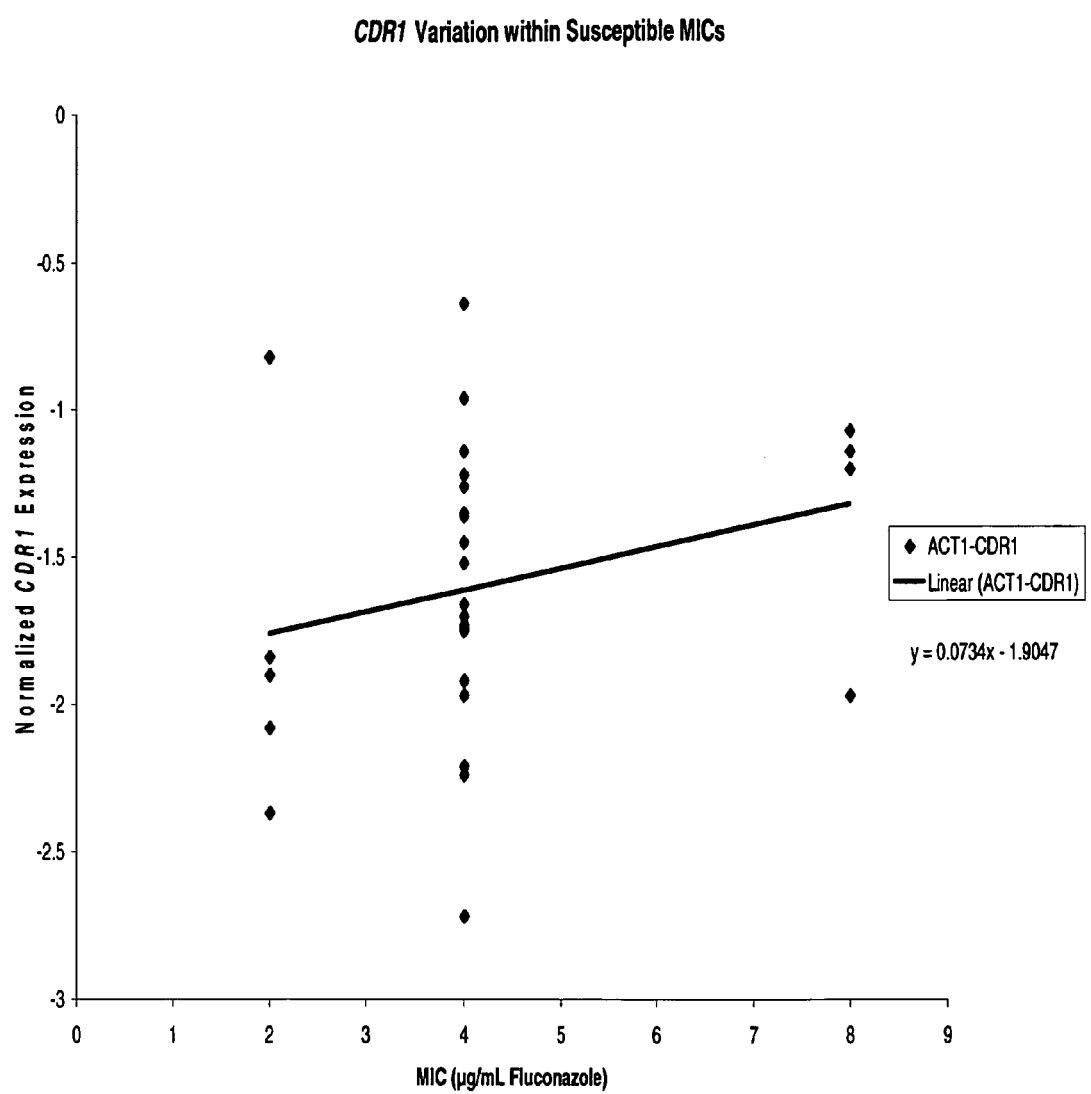
FIG. 4 depicts wide variation of CDR1 mRNA expression levels in clinical isolates that are categorized as azole susceptible based on the microbroth dilution assay and further subdivided into low, medium, and high susceptible MICs (i.e., 2, 4, and 8 µg/mL fluconazole, respectively). The line spanning the three data series demonstrates the linear correlation between normalized CDR1 expression and MIC. Actin was used as a reference in mRNA normalization.

FIG. 4 shows a correlation between CDR1 expression in the susceptible isolates when cultured at 2, 4, and 8 µg/mL fluconazole, respectively. This finding is surprising and we did not expect that CDR1 expression in the azole susceptible group is dependent on the fluconazole (within the dose range between 2-8 µg/mL). This represents the first report of such observation.

Example 6

Establishment of Trend Line-Based Average CDR1 mRNA Level as Baseline for Comparisons Because the CDR1 expression is so widely variable, simply getting an average CDR1 level (from a few clinical isolates) would not provide a consistent and a truly average value, one that can yield a reliable assay in determining azole resistant.

Using the observation that there is a linear correlation between CDR1 and various doses of fluconazole (See, Example 5 and FIG. 4) in susceptible isolates, the present inventors discovered a novel means of obtaining an average CDR1 expression that can serve as a reliable baseline for comparison in a qRT-PCR assay in determining azole resistant.

In this series of study, susceptible isolates were obtained based on a microbroth dilution assay. Then, azole susceptible isolates were cultured in the presence of various doses of fluconazole (i.e., 2, 4, and 8 µg/mL fluconazole) and the CDR1 expression in these isolates was determined. ACT1 was used as reference.

A plot was created between relative CDR1 expression and doses of fluconazole (See, FIG. 4). A trend line was drawn which represented the average level of CDR1 mRNA expression (FIG. 4).

In order to obtain an average level of CDR1 mRNA expression, we selected two isolates for each of the three fluconazole doses in the MIC-based group of susceptible isolates. One normalized CDR1 expression value was from above the trend line and another normalized CDR1 expression value was from below the trend line. CDR1 mRNA values that were chosen were near the trend line value when averaged for that susceptible group. Using the six (6) selected expression levels, an average mRNA level of CDR1 gene was then calculated. This average mRNA level of CDR1 expression was subsequently used as the baseline expression level in comparisons to expression levels determined for biological samples.

In another embodiment, the present invention provides an alternative means to calculate an average mRNA level for CDR1. The values where the trend line intercepts with the MIC doses represents the means for the normalized CDR1 mRNA expression at a particular MIC dose (i.e., 2, 4 or 8 µg/mL). Averaging the means for the normalized CDR1 mRNA expression would provide the average mRNA level needed for calculating the fold-change value.

While a master trend line based on an adequate number of clinical isolates might provide a suitable trend line and average expression level for use in the claimed methods, individuals performing the present method may establish their own trend line to account for variations between equipment, reagents, and platforms used in different laboratories. The use of the independently established trend lines, and the average expression levels based thereon, is considered to be within the scope of the claimed methods.

Example 7

Establishment of an Equation for Calculating Fold-Change in CDR1 mRNA Expression Values We used the following equation to calculate fold-change in CDR1 mRNA expression values for a biological sample (i.e., a clinical isolate):

$$\text{Fold-Change} = 2^{-(\Delta U - \Delta B)},$$

where $\Delta U$=Ct score CDR1 (biological sample)−Ct score ACT1 (biological sample), and where $\Delta B$=average mRNA level for CDR1

This general equation is used to calculate fold change. Note that the average mRNA level for CDR1 is exemplified in Example 6. The equation compares a biological sample to a constant, which in this case is represented by the newly calculated baseline expression level of CDR1. Therefore, by using this equation, a clinical laboratory is able to determine whether a previously untested *Candida glabrata* isolate is resistant or not-resistant by applying the Ct scores obtained from a qRT-PCR on that particular isolate.

Example 8

Confirmation and Validation of the Use of Calculated CDR1 Baseline Expression in qRT-PCR Determination To Accurately Predict Azole Resistant in Clinical Isolates Containing *Candida glabrata*

In this study, we used eight seven (87) clinical isolates, three (3) from each of the twenty nine (29) swabs from each fluconazole susceptibility group were examined for expression of these resistance markers from our clinical *Candida glabrata* cervicovaginal isolates.

Primers and probes (referred to Table 6) were designed for a qRT-PCR assay to measure the expression of CDR1, PDH1, and PDR1, which were each normalized to actin (ACT1) expression which was assayed in the same reaction with each MDR gene. This assay was shown to be highly specific for the targeted organisms as it did not cross-react with a panel of 88 different fungal, bacterial, and viral pathogens, including other *Candida* species.

We obtained a relative mRNA expression of the efflux pumps (i.e., CDR1, PDH1, PDR1 genes) using ACT1 as reference in these clinical isolates.

Upon measuring the expression of the ACT1 gene, we found the expression to be consistent among the susceptible, susceptible dose-dependent, and resistant isolates. The expression of the CDR1, PDH1, and PDR1 genes was consistent among the susceptible isolates (Table 4). Six (6) susceptible isolates (MICs of 8, 8, 4, 4, 2, and 2 µg/ml) were chosen to determine a consistent baseline expression profile for each assay. Non-susceptible isolates were defined by a $\geq$2-fold increase in total target RNA over the susceptible baseline as determined by qRT-PCR.

Ten swabs from each of the three susceptibility groups (S, S-DD, and R) previously tested by microbroth dilution assay (Table 4) were randomly chosen. Three isolates from each swab were used in the qRT-PCR azole susceptibility assay (Table 4). Non-susceptible (S-DD and R) isolates were determined in this assay by a $\geq$2-fold change in any of the three target genes. This resulted in the ability of the qRT-PCR assay to determine non-susceptible isolates with 80% sensitivity, 100% specificity, 100% positive predictive value (PPV) and 71% negative predictive value (NPV).

For determining resistance, a more stringent cut-off of $\geq$3-fold increase in expression of CDR1 alone could be used as the predominant molecular marker for azole resistance with 100% sensitivity, 95% specificity, 91% PPV (positive predictive value, Fisher's test) and 100% NPV (negative predictive value, Fisher's test). All of the isolates tested from the ten (10) resistant swabs resulted in a $\geq$3-fold increased expression of CDR1. The single false positive was a S-DD swab with a MIC of 32 µg/ml. All 10 of the susceptible swabs tested had values $\leq$2-fold for all three molecular markers. The three (3) isolates tested from each of twenty nine (29) swabs demonstrated a consistent susceptibility phenotype as characterized by both MBD and qRT-PCR assays.

Interestingly, swab number 10 contained two (2) isolates that tested susceptible and one isolate that was highly resistant (Table 4, S10a). Although this was a rare occurrence, this supports the need for selecting multiple colonies per swab when performing the qRT-PCR assay.

In sum, this study clearly shows that the correlation between increased expression of CDR1 and increased MIC made it the most suitable candidate as a molecular marker for determining azole resistance in a clinical susceptibility assay. The study further confirms that the use of average mRNA of CDR1 can provide a reliable test in determining azole resistant in a biological sample.

Example 9

Increased CDR1 Expression in Azole Resistant Isolates

In this series of study, we investigated the ability of the assay described herein to determine susceptibility of the thirty (30) clinical isolates mentioned in Example 1 (ten (10) susceptible, ten (10) susceptible-dose dependent, and ten (10) resistant).

Figure 7:
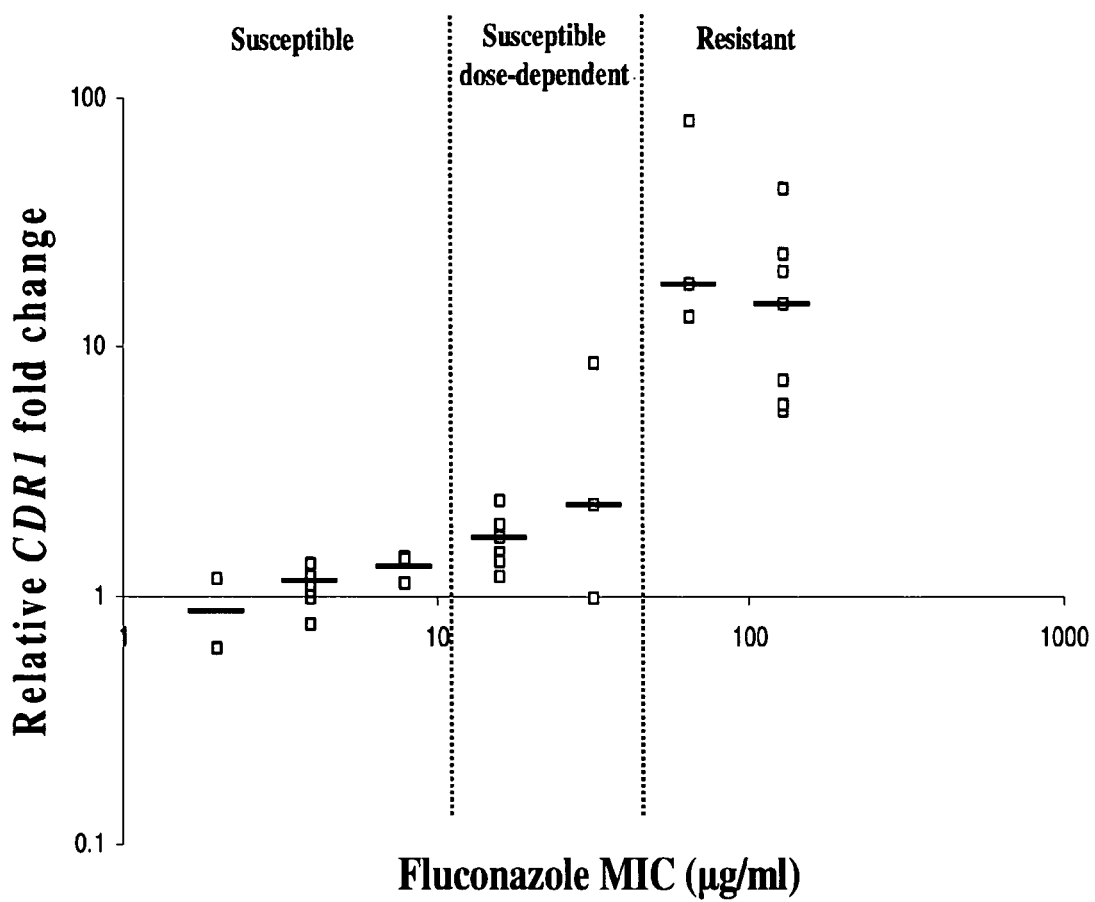
FIG. 7 depicts the relative fold-changes in CDR1 expression for susceptible (S), susceptible dose-dependent (S-DD), and resistant (R) clinical isolates as compared to a baseline value based on a calculated average mRNA level for susceptible isolates. The dashed lines represent the interpretive breakpoints for triazole resistance based on the microbroth dilution assay.

As illustrated in FIG. 7, the fold-change increase of CDR1 vs. MIC data clearly shows that there is a strong relationship between CDR1 up-regulation and clinical resistance. This assay performed with 100% sensitivity and 90% specificity using a 2-fold increase as a resistance cutoff and 100% sensitivity and 95% specificity with a 3-fold cutoff for determining triazole resistance. As such, resistance cutoff points based on either a 2-fold or a 3-fold change in CDR1 expression levels over the calculated baseline is considered to be suitable for use in a diagnostic clinical assay due to the high degree of specificity associated with each. A resistance cutoff point based on a 3-fold change in CDR1 expression levels over the calculated baseline may be advantageous for use in a diagnostic clinical assay where a higher degree of specificity is desired.

We also investigated other MDR genes alone and in combination to determine if they could accurately predict resistance and to confirm that the selection of CDR1 expression was appropriate. The other MDR genes had very low sensitivities when used alone (30% for both PDR1 and PDH1). A combination of all three MDR genes in which up-regulation of any one gene was considered resistant had high sensitivity (100%) but low specificity (75%). If all three (3) MDR genes had to be up-regulated in order to be considered a resistant isolate, there would be 10% sensitivity and 100% specificity. Based on these data, the inventors concluded that CDR1 is the most appropriate choice for a triazole resistance assay.

Example 10

Differential Gene Expression Between the S-DD and R Isolates

Figure 8:
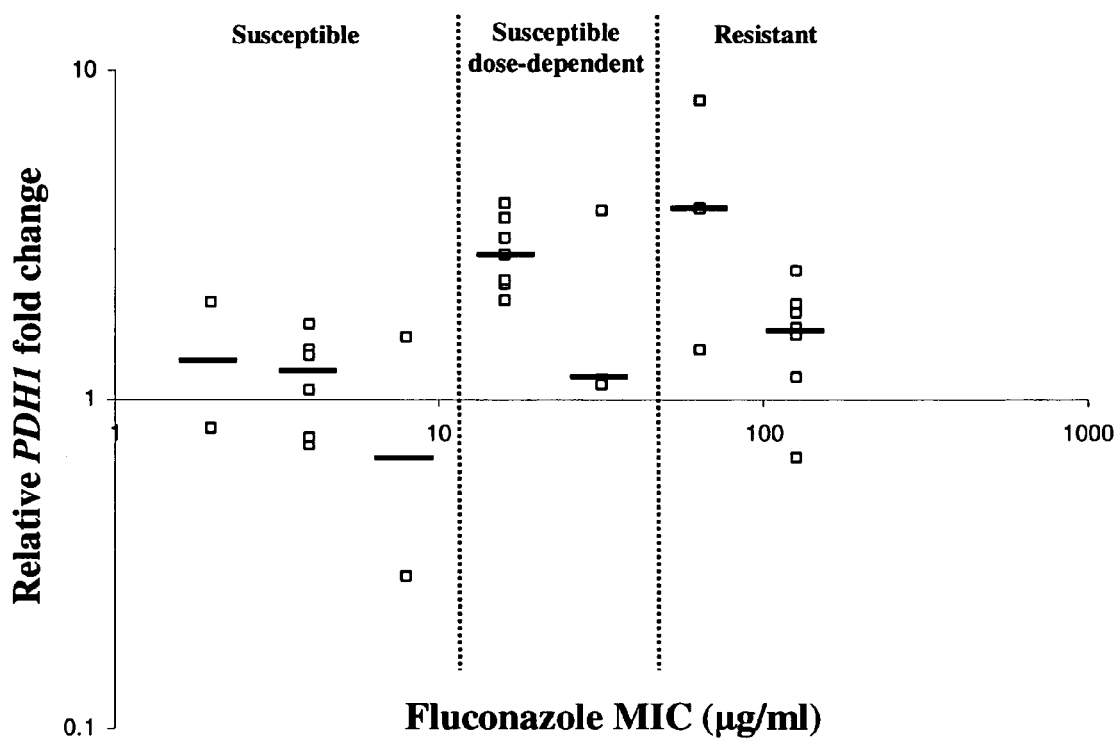
FIG. 8 depicts the relative fold-changes in PDH1 expression for susceptible (S), susceptible dose-dependent (S-DD), and resistant (R) clinical isolates as compared to a baseline value based on a calculated average mRNA level for susceptible isolates.
Figure 9:
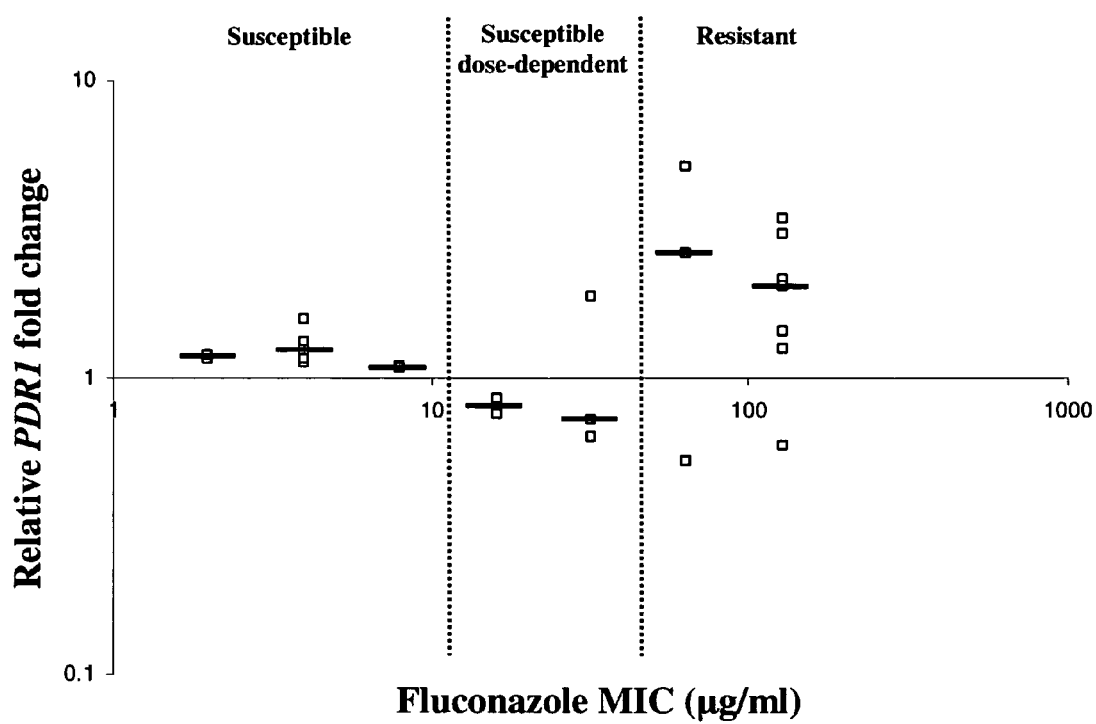
FIG. 9 depicts relative fold-changes in PDR1 expression for susceptible (S), susceptible dose-dependent (S-DD), and resistant (R) clinical isolates as compared to a baseline value based on a calculated average expression level for susceptible isolates.

This study showed a difference in the expression of MDR genes between susceptible dose-dependent (low-level resistance) and resistant (high-level resistance) clinical isolates. The number of R isolates with a $\geq$2-fold increase in gene expression for CDR1, PDH1, and PDR1 was 100, 30, and 30 percent, respectively. Whereas, the number of S-DD isolates with a $\geq$2-fold increase in gene expression for CDR1, PDH1, and PDR1 was 20, 50, and 0 percent, respectively. An increase in CDR1 expression was observed to be proportional to an increase in fluconazole MIC (FIG. 7). Similar patterns of expression were seen for PDR1, the transcriptional regulator (FIG. 8). This data suggests that increased expression of CDR1, potentially under the transcriptional regulation of PDR1, is the predominant mechanism of high-level resistance. However, the greatest number of isolates with elevated expression of PDH1 appears to be in the susceptible dose-dependent isolates (FIG. 9), suggesting that this transporter is involved in low-level resistance.

Example 11

Comparative Studies Using Other Conventional Method

The present method provides a high throughput clinical assay for determining azole resistance by *Candida glabrata* in biological samples while maintaining high sensitivity and specificity when compared to the gold-standard microbroth dilution assay. To demonstrate the effectiveness, we also compared results of the assay to those of several commonly used methods.

SYBR Green qRT-PCR

Hot acidic phenol-chloroform RNA extraction was combined with SYBR Green Buffer and Primers to quantitate the genes of interest studied in a qRT-PCR assay. ACT1 was quantitated in separate reactions for each isolate to provide normalization. This method did not generate results that were consistent with the gold-standard microbroth dilution assay. Both the sensitivity (60%) and specificity (64%) levels of this method were relatively low as compared to those of the claimed methods.

Thus, the failure of this common method (e.g., SYBR Green qRT-PCR), when combined with hot acidic phenol-chloroform RNA extraction, demonstrates the unexpected success of the present invention as a highly sensitive and specific assay for detecting azole resistance in *Candida glabrata*.

Example 12

Comparison of Various RNA Extraction Methods

When RNA was extracted using phenol-chloroform, we observed problems with the use of the isolated RNA in qRT-PCR. It was concluded that the extraction method employing phenol-chloroform did not provide good RNA for the qRT-PCR assay. When phenol-chloroform extracted RNA was used in TaqMan qRT-PCR or multiplex qRT-PCR, it still failed to produce high sensitivity and specificity. Thus, phenol-chloroform RNA extraction remains problematic for these methods.

When the RNA extraction method was switched to the Qiagen RNeasy RNA extraction kit, sensitivity and specificity increased significantly. Qiagen RNeasy contains guanidine thiocyanate and guanidine hydrochloride. When TaqMan multiplex qRT-PCR data is compared for the two RNA extractions, phenol-chloroform had a sensitivity and specificity of 60% and 57%, respectively, while Qiagen RNA extraction had sensitivity and specificity of 100% and 90% using the two-fold cutoff value.

Experimental Reagents and Protocols

A. Media, Drugs and Isolates

The microbroth dilution assays were performed using RPMI 1640 (minus glutamine, and 0.165 M MOPS to pH 7.0) (Sigma, St. Louis, Mo.). BBL CHROMagar plates (BD, Sparks, Md.) were used for *Candida* isolation and speciation in addition to in-house species-specific PCR tests. Drugs were obtained from the following sources: fluconazole (LKT Laboratories, St. Paul, Minn.), miconazole (MP Biomedicals, Inc., Solon, Ohio) and voriconazole (Pfizer, New York, N.Y.). All drugs were dissolved in dimethyl sulfoxide (DMSO) to a final concentration of $\leq 0.5\%$ in all experiments at which *C. glabrata* growth was not affected.

Clinical *Candida glabrata* isolates used in this study were obtained from cervicovaginal swabs submitted to our clinical diagnostic laboratory (Medical Diagnostic Laboratories LLC, Hamilton, N.J.) for PCR-based *Candida* species-specific testing by an evaluating physician (OneSwab®, MDL). Upon receipt, swabs were immediately processed for PCR analysis. Reference strains were obtained from the American Type Culture Collection (Manassas, V.A.) and include: *Candida glabrata* 66032, 90876, and 200918. Identification of *Candida glabrata* species was confirmed using CHROMagar and/or a rapid trehalase test.

B. Isolation of *Candida* Vaginal Isolates

Cervicovaginal swab samples were tested using in-house real-time PCR assays. Samples that tested positive for *Candida glabrata* were selected for analysis on BBL CHROMagar *Candida* plates for additional confirmation. All procedures were completed in a BSL 2 hood under sterile conditions. Samples stored at −20° C. were thawed and vortexed for 5 seconds. The swab was removed from the transport vial and excess transport media was expressed against the interior side of the vial. The swab was used to make a single heavy streak on the CHROMagar plate and then a sterile loop was used to streak for single colonies. Plates were incubated at 35-37° C. for 24 to 48 hours. *Candida* species were identified by coloration and colony morphology on BBL CHROMagar *Candida* plates according to the manufacturer's directions.

C. Microbroth Dilution Assay (Susceptibility Testing)

Protocols for microbroth dilution assays (i.e., susceptibility testing) was performed by MBD according to the Clincial and Laboratory Standards Institute (CLSI) guidelines outlined in M27-A2. Azole antifungals and concentrations tested were fluconazole (2 to 128 µg/ml), voriconazole (8 to 0.125 µg/ml), and miconazole (8 to 0.125 µg/ml). *Candida glabrata* isolates were growth in RPMI 1640 media (minus glutamine, plus 2% glucose, and 0.165M MOPS to pH 7.0) to mid-log phase and cultures were diluted to $5 \times 10^3$ cells/ml in RPMI 1640 medium. Aliquots of 100 µl were distributed to wells of a 96-well flat-bottom plate, except for row A which received 200 µl. Drug was added to row A at the desired concentration (fluconazole, 128 µg/ml, voriconazole 8 µg/ml, and miconazole 8 µg/ml) and then serially two-fold diluted to rows B through G; row H served as a drug-free control. Plates were incubated at 35° C. for 24 and 48 hours. Absorbance at 620 nm was read with a microplate reader (Beckman Coulter, Inc., Fullerton, Calif.); background due to medium was subtracted from all readings.

The MIC was defined as the lowest concentration inhibiting growth at least 80% relative to the drug-free control. Microbroth dilution assays were performed on isolates prior to qRT-PCR and the isolates were separated into corresponding phenyoptyes for qRT-PCR examination. The interpretive breakpoints for susceptibility to triazole (e.g., fluconazole and voriconazole) were described by CLSI and are outlined in Table 5.

D. RNA Isolation

RNA was isolated using the Qiagen RNeasy kit according to the manufacturer's instructions. Briefly, aerated overnight cultures grown in YPD medium at 35° C. were diluted 1:100 and incubated an additional 3 hours to mid-log phase (O.D.$_{600}$=0.4-0.6). Cells were quantified by hemocytometer and $2 \times 10^7$ cells were centrifuged (1,000×g, 5 min) and re-suspended in 100 µl Y1 buffer (86.1 µl Y1 stock [1M sorbitol, 0.1 M EDTA at pH 7.4], 0.4 µl β-mercaptoethanol, and 13.2 µl zymolase [50 units per $1 \times 10^7$ cells]). Cells were subsequently incubated for 30 min at 30° C. at 125 rpm. 350 µl buffer RLT (components, 10 µl (per 1 ml RLT buffer) β-mercaptoethanol) was added, followed by vigorous vortexing. Cellular extracts were centrifuged at full speed for 2 min and supernatants were isolated. 250 µl of 100% ethanol was added, mixed by pipetting, and transferred to RNeasy spin columns [15 seconds at 9,000×g and flow through was discarded]. Columns were washed twice with 700 µl buffer RW1 buffer [spin 15 seconds at 9,000×g and discard flow through] and then with 500 µl of RPE buffer [15 seconds at 9,000×g and discard flow through], then eluted with 50 µl RNAse free H$_2$O. RNA was treated with RQ1 DNAse (Promega, Madison, Wis.).

Quantity and purity were determined by spectrophotometer at absorbance $A_{260}$ to $A_{280}$ (NanoDrop Technologies, Inc., Wilmington, Del.). RNA was diluted to 50 ng/µl and used in qRT-PCR reactions.

E. Primers and Probes

The oligonucleotide primers and probes in this study were synthesized by Integrated DNA Technologies (IDT; Coralville, Iowa) and are listed in Table 6. The dual-labeled oligonucleotide probes were purified by HPLC by the manufacturer.

F. qRT-PCR Analysis

The mRNA quantity of resistance gene markers was measured using a One-Step qRT-PCR on the Stratagene Mx3000P QPCR system (Stratagene, Lajolla, Calif.). qRT-PCR was performed in triplicate with independent amplifications using the same RNA for the gene of interest and the actin housekeeping gene (ACT1) in a duplex reaction. The reaction was performed in a final volume of 25 µl containing 125 ng isolated RNA, 0.6 µM forward and reverse primers for each gene of interest, 0.2 µM probe for each gene of interest (FAM), 0.6 µM ACT1 forward and reverse primers, 0.2 µM ACT1 probe (Cy5) (Table 7), 12.5 µl of Quanta One-Step master mix (2×) (Quanta Biosciences, Gaithersburg, Md.), 6.5 µl of nuclease-free water, and 0.5 µl of Quanta Escript One-Step reverse transcriptase.

The PCR conditions consisted of an initial incubation at 50° C. for 10 min, then 94° C. for 3 min, followed by 35 cycles of denaturation at 94° C. for 20 sec and annealing/extension at 51° C. for 1 min. (Table 8). The fluorescence acquisition was performed at the end of each cycle immediately following the annealing/extension step. Negative controls consisted of the substitution of nuclease and pyrogen-free water for RNA. All expression levels were normalized to ACT1. The $C_T$ value of ACT1 was subtracted from that of the gene of interest to obtain a $\Delta C_T$ value. The average $\Delta C_T$ value of a panel of susceptible clinical isolates (n=6) was subtracted from the ACT value of each sample to obtain a $\Delta\Delta C_T$ value. The gene expression level relative to the panel of susceptible clinical isolates was expressed as $2^{-\Delta\Delta C_T}$.

TaqMan Multiplex qRT-PCR was performed using the master mix described below (Table 7). Primers and probes for CDR1, ACT1, PDR1, and PDH1 are listed in Table 6 (SEQ ID NOs: 1-12, respectively) above. The qRT-PCR reactions included PDR1+ACT1; CDR1+ACT1; and PDH1+ACT1. The qRT-PCR used the Strategene Mx3000p System, reading gene of interest (GOI) (e.g., CDR1) on FAM channel and ACT1 normalizer on Cy5 channel.

The thermal profile for the PCR steps is outlined below (Table 8). CDR1, PDR1, and PDH1 mRNA expression was calculated using ACT1 (beta-actin gene, often used as a control because its expression is at a constant level) as a control.

G. Statistical Analysis

All statistical analyses were performed using GraphPad Instat version 3.0b for Macintosh (GraphPad Software, San Diego, Calif.). Contingency analyses and Fisher's exact tests were used to determine genotypic and phenotypic correlations. A two-tailed p value of less than or equal to 0.05 was considered statistically significant.

The foregoing detailed description provides exemplary embodiments of the invention and includes the best mode for practicing the invention. The description and illustration of embodiments is intended only to provide examples of the invention and not to limit the scope of the invention, or its protection, in any manner. All patents, patent applications, publications and other materials cited herein are hereby incorporated by reference in their entirety.

TABLE 1

Susceptibility of 175 Candida glabrata Clinical Isolates

| | No. (%) of isolates | | |
|---|---|---|---|
| C. glabrata (175) | S | S-DD | R |
| Fluconazole | 54 (30.9%) | 74 (42.2%) | 47 (26.9%) |
| Voriconazole [a] | 109 (62.3%) | 24 (13.7%) | 42 (24.0%) |
| Miconazole [b] | 175 (100.0%) | 0 (0.0%) | 0 (0.0%) |

S, susceptible; S-DD, susceptible dose dependent; R, resistant. Values were as determined by the CLSI M27-A2 broth microdilution reference method
[a] Proposed breakpoints were used to determine interpretive categories for voriconazole.
[b] Proposed breakpoints were used to determine interpretive categories for miconazole.

TABLE 2

Use of Low CDR1 mRNA Level as Baseline in Determining Azole Resistant in Clinical Isolates: Comparison to Microbroth Dilution Assay

| Azole Resistant Assays | Clinical Isolates (30 Total) | |
|---|---|---|
| Microbroth Dilution Assay | R: 10 S and S-DD: 20 | |
| When based on calculated CDR1 expression level ≧ 2-fold | | |
| qRT-PCR Assay Using a Low CDR1 mRNA Value | R: 20 S and S-DD: 10 | Sensitivity: 1.0 Specificity: 0.5 |
| When based on calculated CDR1 expression level ≧ 3-fold | | |
| qRT-PCR Assay Using a Low CDR1 mRNA Value | R: 12 S and S-DD: 18 | Sensitivity: 1.0 Specificity: 0.9 |

TABLE 3

Use of High CDR1 mRNA Level as Baseline in Determining Azole Resistant in Clinical Isolates: Comparison to Microbroth Dilution Assay

| Azole Resistant Assays | Clinical Isolates (30 Total) | |
|---|---|---|
| Microbroth Dilution Assay | R: 10 S and S-DD: 20 | |
| When based on calculated CDR1 expression level ≧ 2-fold | | |
| qRT-PCR Assay Using a High CDR1 mRNA Value | R: 8 S and S-DD: 22 | Sensitivity: 0.8 Specificity: 1.0 |
| When based on calculated CDR1 expression level ≧ 3-fold | | |
| qRT-PCR Assay Using a High CDR1 mRNA Value | R: 5 S and S-DD: 25 | Sensitivity: 0.5 Specificity: 1.0 |

TABLE 4

Fold-change in CDR1, PDH1, and PDR1 Gene Expression Compared to a Susceptible Panel as Determined by qRT-PCR

| Swab[a] | MIC (µg/ml) | Fold-change CDR1 | PDH1 | PDR1 |
|---|---|---|---|---|
| S1 | 8 | 1.43 ± 0.06 | 0.29 ± 0.26 | 1.08 ± 0.12 |
| S2 | 4 | 0.97 ± 0.16 | 1.41 ± 0.12 | 1.12 ± 0.17 |
| S3 | 4 | 1.19 ± 0.34 | 1.36 ± 0.18 | ND |
| S4 | 2 | 0.61 ± 0.13 | 0.81 ± 0.21 | 1.15 ± 0.17 |
| S5 | 4 | 1.38 ± 0.20 | 0.73 ± 0.29 | 1.56 ± 0.25 |
| S6 | 4 | 1.04 ± 0.16 | 0.76 ± 0.15 | 1.32 ± 0.08 |
| S7 | 4 | 0.76 ± 0.16 | 1.70 ± 0.30 | 1.15 ± 0.17 |
| S8 | 4 | 1.10 ± 0.12 | 1.06 ± 0.08 | ND |
| S9 | 2 | 1.17 ± 0.53 | 1.96 ± 0.69 | 1.19 ± 0.12 |
| S10[b] | 8 | 1.40 ± 0.85 | 1.55 ± 0.28 | 1.09 ± 0.69 |
| S11 | 16 | 1.13 ± 0.70 | 3.09 ± 0.49 | ND |
| S12 | 16 | 1.49 ± 0.14 | 2.76 ± 1.26 | ND |
| S13 | 16 | 2.39 ± 0.28 | 2.25 ± 0.49 | ND |
| S14 | 16 | 1.94 ± 0.53 | 1.99 ± 0.68 | 0.84 ± 0.32 |
| S15 | 32 | 2.33 ± 0.43 | 1.11 ± 0.09 | 0.72 ± 0.25 |
| S16 | 16 | 1.19 ± 0.20 | 3.95 ± 0.83 | ND |
| S17 | 16 | 1.70 ± 0.79 | 3.56 ± 1.15 | 0.75 ± 0.27 |
| S18 | 16 | 1.37 ± 0.21 | 2.29 ± 0.29 | ND |
| S19 | 32 | 0.98 ± 0.18 | 1.15 ± 0.14 | 0.63 ± 0.30 |
| S20 | 32 | 8.60 ± 0.89 | 3.73 ± 0.16 | 1.87 ± 0.11 |
| S21 | 128 | 20.10 ± 2.10 | 1.64 ± .017 | 1.25 ± 0.06 |
| S22 | 128 | 23.44 ± 2.23 | 1.57 ± 0.26 | 1.42 ± 0.05 |
| S23 | 128 | 7.23 ± 0.89 | 2.45 ± 0.33 | 0.59 ± 0.15 |
| S24 | 128 | 5.81 ± 0.63 | 0.66 ± 0.07 | 2.02 ± 0.94 |
| S25 | 64 | 17.85 ± 2.75 | 1.41 ± 0.36 | 2.62 ± 0.41 |
| S26 | 128 | 42.63 ± 3.83 | 1.17 ± 0.15 | 3.43 ± 0.50 |
| S27 | 64 | 80.23 ± 22.98 | 3.78 ± 0.29 | 5.12 ± 1.08 |
| S28 | 128 | 14.67 ± 0.81 | 1.94 ± 0.38 | 2.14 ± 0.76 |
| S29 | 64 | 13.05 ± 6.89 | 8.07 ± 3.76 | 0.52 ± 0.16 |
| S10[b] | 128 | 5.5 ± n.a. | 1.83 ± n.a. | 3.01 ± n.a |

[a] Fold change represents the average ± standard deviation of three isolates from each swab.
[b] Two susceptible and one resistant clinical isolates were recovered from swab 10.
ND = Not detected
n.a. = not applicable for a single isolate.

TABLE 5

Phenotypes and MIC Cutoff for *Candida glabrata*

| Phenotypes | MIC Cutoff |
|---|---|
| Resistant (R) | ≧64 µg/mL Fluconazole |
| | ≧4 µg/mL Voriconazole |
| Susceptible Dose-Dependent (S-DD) | 16-32 µg/mL Fluconazole |
| | 2 µg/mL Voriconazole |
| Susceptible (S) | ≦8 µg/mL Fluconazole |
| | ≦1 µg/mL Voriconazole |

TABLE 6

Primers and TaqMan Probes

| Primers or Probes | Oligonucteotide Sequences (SEQ ID NO) |
|---|---|
| CDR1 Forward | TTAAAAGTTCAAGCCAGTATTTCC (SEQ ID NO: 1) |
| CDR1 Reverse | AAATTTGATAACCATCGTAAAGCA (SEQ ID NO: 2) |
| CDR1 probe (FAM) | CGCTGCTGCTACTGTGGCTATCT (SEQ ID NO: 3) |
| ACT1 Forward | CGCTTTGGACTTCGAACAAGAA (SEQ ID NO: 4) |
| ACT1 Reverse | GTTACCGATGGTGATGACTTGAC (SEQ ID NO: 5) |
| ACT1 probe (Cy5) | AACCGCTGCTCAATCTTCCTCCAT (SEQ ID NO: 6) |
| PDR1 Forward | TACATGGAACATCTGTTGCTTCTT (SEQ ID NO: 7) |
| PDR1 Reverse | CGACTCTTCATAGCCGACGT (SEQ ID NO: 8) |
| PDR1 probe (FAM) | GAAGAACAGCTTGCTCTCGACGA (SEQ ID NO: 9) |
| PDH1 Forward | CAGACCCGGTTCCGGTTGTA (SEQ ID NO: 10) |
| PDH1 Reverse | CGGTAGTGCTTCTTGATCTCGTT (SEQ ID NO: 11) |
| PDH1 probe (FAM) | ACGCTGCTGAAGTCCATCTCCTCG (SEQ ID NO: 12) |

TABLE 7

Master Mix for Use in TaqMan Multiplex qRT-PCR

| Master Mix Ingredients | Volume |
|---|---|
| Master mix | 1x |
| Quanta One-Step buffer (2x) | 12.5 µl |
| Nuclease-free water | 6.5 µl |
| Forward Primers (gene of interest + ACT1) (30 µM) | 0.5 µl |
| Reverse Primers (gene of interest + ACT1) (30 µM) | 0.5 µl |
| TaqMan Probes (gene of interest (FAM) + ACT1 (Cy5)) (10 µM) | 0.5 µl |
| Quanta Escript Reverse Transcriptase | 0.5 µl |
| RNA (50 ng/µl stock) | 2.5 µl |
| Total Volume | 25 µl |

TABLE 8

Thermal profile for use in TaqMan Multiplex qRT-PCR

| Steps | Temperature (° C.) | Time |
|---|---|---|
| 1 | 50° C. | 10 min |
| 2 | 94° C. | 3 min |
| 3* | 94° C. | 20 min |
| 4* | 51° C. | 1 min |

*Repeat steps 3-4 thirty times.

What is claimed is:

1. A method for determining azole resistance in *Candida glabrata*, comprising the steps of
   a) obtaining a biological sample containing *Candida glabrata*;
   b) isolating RNA from said biological sample;
   c) performing qRT-PCR to determine mRNA level of CDR1 gene of said biological sample; and
   d) comparing said mRNA level in step (c) with an average mRNA level to obtain a fold-change value, said average mRNA level is obtained by a process, said process comprises the steps of:
      (i) obtaining a plurality of azole susceptible isolates of *Candida glabrata*, wherein said azole susceptible isolates are determined using a microbroth dilution assay conducted at a plurality of azole MIC concentrations between about 2 μg/mL to about 8 μg/mL;
      (ii) performing qRT-PCR to determine normalized mRNA level of CDR1 gene of said azole susceptible isolates for each azole MIC concentration;
      (iii) generating a trend line between said normalized CDR1 expression level in step (ii) and said azole MIC concentrations in step (i);
      (iv) calculating the mean of at least one normalized CDR1 expression level above said trend line and at least one normalized CDR1 expression level below said trend line to obtain an average normalized CDR1 expression level for each azole MIC concentration; and
      (v) calculating the mean of said average normalized CDR1 expression levels to obtain an average mRNA level, wherein a $\geq$2-fold change value is indicative of azole resistance of said *Candida glabrata* present in said biological sample, and wherein said method having a sensitivity of $\geq$90% and a specificity $\geq$90%.

2. The method of claim 1, wherein said biological sample in step (a) is obtained from a cervicovaginal swab, blood, or urine.

3. The method of claim 1, wherein said biological sample in step (a) is obtained from a cervicovaginal swab.

4. The method of claim 1, wherein said isolating step is performed using a reagent selected. from the group consisting of guanidine thiocyanate and guanidine hydrochloride.

5. The method of claim 1, wherein said performing step (c) is TaqMan qRT-PCR or multiplex qRT-PCR.

6. The method of claim 1, wherein said performing step (c) is performed using a forward primer and a reverse primer, wherein said forward primer has a nucleotide sequence set forth in SEQ ID NO: 1, and said reverse primer has a nucleotide sequence set forth in SED ID NO: 2.

7. The method of claim 6, where said performing step (c) is performed further using a probe, said probe having a nucleotide sequence set forth in SEQ ID NO: 3.

8. The method of claim 1, wherein said performing step (ii) is performed using a forward primer and a reverse primer, wherein said forward primer has a nucleotide sequence set forth in SEQ ID NO: 1, and said reverse primer has a nucleotide sequence set forth in SED ID NO: 2.

9. The method of claim 8, where said performing step (ii) is performed further using a probe, said probe having a nucleotide sequence set forth in. SEQ ID NO: 3.

10. The method of claim 1, wherein said azole is a triazole.

11. The method of claim 10, wherein said triazole is selected from the group consisting of fluconazole, voriconazole, posaconazole and itraconazole.

12. The method of claim 1, wherein said microbroth dilution assay in step (i) is conducted at three azole concentrations.

13. The method of claim 12, wherein said azole concentration comprises 2, 4 and 8 μg/mL, of fluconazole.

14. The method of claim 1, wherein said generating step in step (iii) is performed using actin as a reference gene.

15. The method of claim 1, wherein said fold-change value is ≧3-fold.

16. The method of claim. 15, wherein said method has a sensitivity of ≧95% and a specificity of≧95%.

17. A method for determining azole resistance in *Candida glabrata*, comprising the steps of
   a) obtaining a biological sample containing *Candida glabrata*;
   b) isolating RNA from said biological sample;
   c) performing qRT-PCR to determine mRNA level of CDR1 gene of said biological sample; and
   d) comparing said mRNA level in step (c) with an average mRNA level to obtain a fold-change value, said average mRNA level is obtained by a process, said process comprises the steps of
      (i) obtaining a plurality of azole susceptible isolates of *Candida glabrata*, wherein said azole susceptible isolate is determined using a microbroth dilution assay conducted at fluconazole MIC concentrations of 2 μg/mL, 4 μg/mL, and 8 μg/mL;
      (ii) performing qRT-PCR to determine mRNA level of CDR1 gene of said azole susceptible isolates for each MIC;
      (iii) generating a trend line between normalized CDR1 expression level in step (ii) and said fluconazole MIC concentrations in step (i);
      (iv) calculating the mean of at least one normalized CDR1 expression level above said trend line and at least one normalized CDR1 expression level below said trend line to obtain an average normalized CDR1 expression level for each fluconazole concentration to obtain an averaged normalized CDR1 expression level for each azole concentration; and
      (v) calculating the mean of said average normalized CDR1 expression levels to obtain said average mRNA level, wherein a≧2-fold change value is indicative of azole resistance of said *Candida glabrata* present in said biological sample, and wherein said method having a sensitivity of ≧90% and a specificity ≧90%.

* * * * *